US007879008B2

(12) United States Patent
Haury et al.

(10) Patent No.: US 7,879,008 B2
(45) Date of Patent: Feb. 1, 2011

(54) CONTROL DEVICE FOR A FLUID DELIVERY SYSTEM

(75) Inventors: John A. Haury, Sewickley, PA (US); James M. Gimbel, Delmont, PA (US); Matthew J. Leroch, IV, Pittsburgh, PA (US); Paul J. Miller, Pittsburgh, PA (US); Gerald W. Callan, Cranberry Township, PA (US); Richard C. Morton, Allison Park, PA (US); Ralph E. Kopacko, Irwin, PA (US); Jennie Kwo, Cambridge, MA (US); Luis A. Padraza, Roxbury, MA (US); Roderick H. Beaulieu, Cumberland, RI (US); Russell W. Wade, Laguna Miguel, CA (US); Milan V. Trcka, Northridge, CA (US); Mark Evan Whitebook, Capistrano Beach, CA (US)

(73) Assignee: MEDRAD, Inc., Indianola, PA (US)

( * ) Notice: Subject to any disclaimer, the term of this patent is extended or adjusted under 35 U.S.C. 154(b) by 1031 days.

(21) Appl. No.: 11/085,616

(22) Filed: Mar. 21, 2005

(65) Prior Publication Data

US 2005/0273056 A1    Dec. 8, 2005

Related U.S. Application Data

(60) Provisional application No. 60/560,496, filed on Apr. 8, 2004, provisional application No. 60/627,764, filed on Nov. 12, 2004.

(51) Int. Cl.
*A61M 1/00* (2006.01)

(52) U.S. Cl. .................... 604/151; 604/890.1; 604/131

(58) Field of Classification Search .................. 604/151, 604/131, 152–155, 246–247, 283–284, 890.1–892.1
See application file for complete search history.

(56) References Cited

U.S. PATENT DOCUMENTS

| 4,246,452 | A | * | 1/1981 | Chandler | .................... 200/5 A |
|---|---|---|---|---|---|
| 4,370,982 | A | | 2/1983 | Reilly | |
| 4,559,036 | A | | 12/1985 | Wunsch | |
| 4,710,166 | A | | 12/1987 | Thompson et al. | |
| 4,925,444 | A | | 5/1990 | Orkin et al. | |

(Continued)

FOREIGN PATENT DOCUMENTS

CA          2045070          2/1992

*Primary Examiner*—Kevin C Sirmons
*Assistant Examiner*—Phillip Gray
(74) *Attorney, Agent, or Firm*—Gregory L. Bradley

(57) ABSTRACT

The control device is used to control delivery of fluid from a fluid delivery system during a medical injection procedure. The fluid delivery system includes an injector adapted to actuate a syringe used to deliver the injection fluid to a patient. The control device is operatively associated with the injector for controlling discrete flow rates of injection fluid delivered to the patient. The control device includes a housing and an actuator associated with the housing. An electronic substrate is disposed within the housing and comprises a conductive pattern. The actuator is adapted for operative association with the conductive pattern. The conductive pattern includes a plurality of predetermined digital values corresponding to discrete flow rates of injection fluid to be delivered by the injector, such that when the actuator is actuated the actuator operatively associates with the conductive pattern for transmitting the digital values to the injector.

39 Claims, 9 Drawing Sheets

U.S. PATENT DOCUMENTS

| | | |
|---|---|---|
| 5,021,046 A | 6/1991 | Wallace |
| 5,152,776 A | 10/1992 | Pinchuk |
| 5,199,604 A | 4/1993 | Palmer et al. |
| 5,273,537 A | 12/1993 | Haskvitz et al. |
| 5,460,609 A | 10/1995 | O'Donnell |
| 5,515,851 A | 5/1996 | Goldstein |
| 5,573,515 A | 11/1996 | Wilson et al. |
| 5,800,397 A | 9/1998 | Wilson et al. |
| 5,806,519 A | 9/1998 | Evans, III et al. |
| 5,807,349 A | 9/1998 | Person et al. |
| 5,840,026 A | 11/1998 | Uber, III et al. |
| 5,882,343 A | 3/1999 | Wilson et al. |
| 5,885,216 A | 3/1999 | Evans, III et al. |
| 5,916,165 A | 6/1999 | Duchon et al. |
| 5,988,587 A | 11/1999 | Duchon et al. |
| 6,099,502 A | 8/2000 | Duchon et al. |
| 6,221,045 B1 | 4/2001 | Duchon et al. |
| 6,293,958 B1 | 9/2001 | Berry et al. |
| 6,344,030 B1 | 2/2002 | Duchon et al. |
| 6,361,528 B1 | 3/2002 | Wilson et al. |
| 6,442,418 B1 | 8/2002 | Evans, III et al. |
| 6,447,481 B1 | 9/2002 | Duchon et al. |
| 6,626,862 B1 | 9/2003 | Duchon et al. |
| 6,656,157 B1 * | 12/2003 | Duchon et al. ............... 604/131 |
| 6,669,679 B1 | 12/2003 | Savage et al. |
| 6,731,971 B2 | 5/2004 | Evans, III et al. |
| 6,746,427 B2 | 6/2004 | Duchon et al. |
| 6,752,789 B2 | 6/2004 | Duchon et al. |
| 6,880,808 B2 | 4/2005 | McPeak et al. |
| 6,889,074 B2 | 5/2005 | Uber, III et al. |
| 2002/0183616 A1 | 12/2002 | Toews et al. |
| 2004/0092885 A1 | 5/2004 | Duchon et al. |

\* cited by examiner

CONTROL DEVICE FOR A FLUID DELIVERY SYSTEM

CROSS REFERENCE TO RELATED APPLICATION

The present application claims the benefit of U.S. Provisional Application Ser. No. 60/560,496 filed on Apr. 8, 2004, and U.S. Provisional Application Ser. No. 60/627,764, filed on Nov. 12, 2004, the disclosures of which are incorporated herein by reference in their entirety.

BACKGROUND OF THE INVENTION

1. Field of the Invention

The present invention relates generally to control devices for controlling operation of fluid-supplying machines or apparatus used in medical procedures such as angiography and, further, to hand-held control devices for controlling the flow rate of fluids, such as contrast media or common flushing agents, injected into a patient during medical procedures, such as angiography.

2. Description of Related Art

Angiography is a procedure used in the detection and treatment of abnormalities or restrictions in blood vessels. During angiography, a radiographic image of a vascular structure (i.e., blood vessel) is obtained by injecting radiographic contrast material, also referred to as contrast media, through a catheter into a vein or artery. X-rays are passed through the region of the body in which the contrast media is concentrated. The X-rays are absorbed by the contrast material, causing a radiographic outline or image of the blood vessel containing the contrast media. The X-ray's images of the blood vessel filled with the contrast media are usually recorded onto film or videotape and are displayed on a fluoroscope monitor.

Many angiographic procedures, in particular coronary angiography and especially coronary vascular interventional procedures such as angioplasty, require frequent intermittent injections of contrast media. The contrast media is administered in varying volumes as well as modulated strengths and time durations. The intermittent contrast media injections are critical for optimal positioning of guiding catheters at the targeted blood vessels, positioning of guide wires to and through the targeted areas during catheter interventions (e.g. percutaneous transluminal coronary angioplasty), and for assessment of the results of such interventional procedures.

During angiography, after a physician places the angiographic catheter into a vein or artery, the angiographic catheter is connected to either a manual or an automatic contrast media injection mechanism. A typical manual contrast media injection mechanism includes a syringe and a catheter connection. The user of the manual contrast media injection mechanism adjusts the rate and volume of injection by altering the manual actuation force applied to the plunger of the syringe.

Automatic contrast media injection mechanisms typically involve a syringe connected to a linear actuator. The linear actuator is connected to a motor, which is controlled electronically. The operator enters into the electronic control a fixed volume of contrast media and a fixed rate of injection. There is typically no interactive control between the operator and the mechanism, except to start or stop the injection. A change in flow rate occurs by stopping the mechanism and resetting the parameters.

Recent improvements in the radiographic imaging field have attempted to apply software and hardware interfaces to automatic contrast media injection mechanisms to provide variable flow rate and fixed flow rate modes to the operator. Additionally, the delivery of common flushing agents, such as saline, may also be controlled using the software/hardware interfaces. One such angiographic control device is disclosed in U.S. Pat. No. 5,515,851 to Goldstein. The Goldstein patent discloses the use of a microchip control device in the form of an angiographic control pad device designed to facilitate finger touch modulation of flow rate, volume, and duration of contrast media injection into a patient during an angiographic procedure. The control finger pad device allows the operator to control the aforementioned parameters during an injection procedure by altering the duration and extent of fingertip depression on the finger pads.

Another control device used to provide variable flow rate control to an operator of an automatic contrast media injection mechanism is disclosed in U.S. Pat. No. 5,916,165 to Duchon et al. This reference discloses a hand-held pneumatic control device that interfaces with and controls a fluid supply or injection mechanism. The hand-held control device is further adapted to control dispensement of saline injected into the patient during the angiographic procedure. The hand-held control device is generally adapted to be responsive to fluid pressure within the device. The control device includes a pressure control member adapted to selectively change fluid pressure within the pressure control member based on inputs from the operator. In one embodiment, the control device is provided with one or more internal air bladders having a volume that selectively adjusts to change the fluid pressure within the air bladders based on operator inputs. Internal sensors are provided to monitor the volume changes of the air bladders, and generate control signals based on the volume changes.

U.S. Pat. No. 5,988,587, also to Duchon et al., discloses another version of a hand-held control device for an automatic contrast media injection mechanism. This reference discloses a hand-held control device that includes two opposing and spaced-apart handles. A resilient attachment member connects the two handles. The resilient attachment member is configured to allow the first handle to move with respect to the second handle in response to operator inputs. The control device includes a sensor attached to the first handle for producing a variable control signal indicative of the distance between the first handle and the second handle.

Yet another hand-held control device is disclosed in U.S. Pat. No. 6,221,045 to Duchon et al. This reference discloses a hand-held control device that generates a control signal that is continuously variable according to continuously varying movement of a user's hand on the hand-held control. The control signal is continuously variable and sustainable at any value between preset maximum and minimum values corresponding to maximum and minimum contrast media discharge flow rates.

As automatic contrast media/fluid injection mechanisms and systems become more complex, it is desirable to interface with such mechanisms and systems on a digital level to afford more control over the medical injection procedures performed with such devices. The foregoing examples of hand-held control devices provide a certain amount of control over such procedures by offering the operator of the contrast media/fluid injection mechanism or system a variable flow rate mode of operating the mechanism or system. However, there is room for improvement in the field of control devices for controlling or operating contrast media/fluid injection mechanisms or systems, for example by providing a control device that may interface with such mechanisms or systems on a truly digital level, while providing accurate flow rate control of contrast media injection and saline flush control. Additionally, there is a need for a hand-held control device that is simple to use, for example, having an intuitive look and feel of operation for the operator. Further, a need exists for a hand-held control device that is simple and inexpensive to manufacture, so that the device itself may be disposable after a preset number of uses.

SUMMARY OF THE INVENTION

Generally, the present invention is a fluid delivery system for use in medical injection procedures that includes a control device for controlling flow rates of fluid delivered from the fluid delivery system to a patient. The fluid delivery system typically includes an injector, for example a powered injector, for delivering fluid to the patient. The control device is generally adapted to control flow rates of fluid delivered by the injector to the patient. In particular, the control device is adapted to provide an operator of the control device with the ability to vary the flow rates of fluid from the injector.

The fluid delivery system and control device may be used in medical injection procedures, such as angiography. In such procedures, as indicated previously, an injector, either manual or powered, is used to deliver fluids, particularly contrast media, under pressure to a patient. Typically, the patient is connected to a syringe associated with the injector by a catheter. The contrast media is injected into the patient upon actuation of the injector. The control device of the present invention is generally adapted to control the injection fluid flow rate to the patient from the injector, for example a powered injector. Thus, the control device provides the operator of a powered injector with a variable flow rate mode to deliver contrast media at discrete flow rates desired by the operator, who is typically a medical practitioner.

Additionally, the control device is generally adapted to control the delivery of additional injection fluids beyond contrast media. For example, it is common to supply saline to the patient during certain aspects of injection procedures, such as angiography. The control device is further adapted to start and stop the flow of an additional fluid, such as saline, to the patient when commanded by the operator. Moreover, the control device of the present invention may be configured to be hand-held and may be ergonomically designed to fit comfortably within the human hand. Further, the control device may be provided as a disposable device, typically used for only a certain number of procedures before being discarded.

The fluid delivery system according to the present invention generally includes an injector that may be adapted to actuate a syringe used to deliver an injection fluid to a patient, and a control device operatively associated with the injector, either directly or indirectly, for controlling flow rates of the injection fluid delivered to the patient. The control device generally includes a housing and an actuator associated with the housing. The control device further includes an electronic substrate disposed within the housing. The electronic substrate comprises a conductive pattern, defined or formed thereon. The actuator is adapted for operative association with the conductive pattern when actuated by a user. The conductive pattern may comprise a plurality of predetermined digital values corresponding to discrete flow rates of injection fluid to be delivered by the injector, such that when the actuator is actuated, the actuator operatively associates with the conductive pattern and transmits the digital values to the injector.

The actuator may be movably associated with the housing for operatively associating with the conductive pattern. The digital values may be arranged such that the discrete flow rates are linearly proportional to distance of movement of the actuator. Additionally, the digital values may be arranged such that the discrete flow rates incrementally increase with distance of movement of the actuator. The incremental increase may comprise 5%, 10%, 20% or any desired incremental increase with each digital value. The digital values typically include at least a first digital value corresponding to no movement of the actuator and a 0% (i.e., no) discrete flow rate, and a last digital value corresponding to a maximum movement of the actuator and a 100% (i.e., full) discrete flow rate. The last digital value may correspond to a maximum possible flow rate from the injector.

The actuator may be movably associated with the housing for operatively associating with the conductive pattern. The actuator may comprise an actuating member and a contact adapted to operatively associate with the conductive pattern. The contact may be in the form of a contact roller adapted to operatively associate with the conductive pattern. The roller may be formed of electrically conductive resilient material, and may be biased into engagement with the electronic substrate. The contact may also be in the form of a contact plate having contact fingers adapted to operatively associate with the conductive pattern. The actuating member may be slidably associated with the electronic substrate.

The contact may be adapted to sequentially access the digital values of the conductive pattern when the actuating member is moved relative to the housing. A biasing member may further be associated with the actuating member for biasing the actuating member to a neutral position relative to the housing. The biasing member may act on the actuating member such that the user of the control device experiences increasing tactile resistance as the actuating member is moved relative to the housing. The biasing member may be further adapted to provide tactile resistance proportional to distance of movement of the actuator relative to the housing.

The electronic substrate and/or housing may comprise sound producing structures positioned to be engaged by the actuator for audibly indicating movement of the actuator relative to the housing.

The control device may be operatively connected to the injector via a fluid control module associated with the injector. The control device may further comprise a secondary actuator adapted to transmit a secondary fluid actuation signal to, for example, the fluid control module upon actuation. The secondary actuator may comprise a control button operatively associated with the electronic substrate for initiating the secondary fluid actuation signal.

A data communication cable may be associated with the electronic substrate for transmitting the digital values to the injector, either directly or indirectly. The data communication cable may be adapted to removably connect the control device with the injector, either directly or indirectly.

The housing of the control device may be a multi-piece housing, including at least a first portion and a second portion. The first portion and second portion may be permanently joined together, for example, bonded together with an adhesive. The housing may be sized and shaped to be hand-held. A disposable sheath may enclose the respective pieces or portions forming the housing of the control device.

The present invention is also a method of controlling a fluid delivery system using the control device described generally hereinabove. The method may include operatively connecting the control device to the injector, with the control device adapted to control discrete flow rates of the injection fluid to be delivered by the injector to the patient, and actuating the control device to transmit one or more predetermined digital values to the injector to control the discrete flow rates of the injection fluid delivered by the injector.

The control device, as indicated previously, may include an actuator, and an electronic substrate comprising a conductive pattern. The actuator may be adapted for operative association with the conductive pattern, and the conductive pattern may comprise a plurality of predetermined digital values corresponding to the discrete flow rates of the injection fluid to be delivered by the injector, such that the step of actuating the control device may comprise the actuator operatively associating with the conductive pattern to transmit one or more predetermined digital values to the injector The actuator may be movable relative to the conductive pattern, such that the step of actuating the control device may comprise moving the actuator relative to the conductive pattern. The actuator may comprise a contact operatively associated with the conductive pattern, such that when the actuator is moved relative to the conductive pattern the contact operatively contacts the conductive pattern. The contact may sequentially access the digital values when the actuator is moved relative to the conductive pattern. The contact may operatively contact the conductive pattern by rolling along the surface of the conductive pattern. The method may further comprise audibly indicating movement of the actuator relative to the conductive pattern.

The method may further comprise discontinuing actuation of the control device, for example, by releasing the actuator, such that the biasing member returns the actuator to a substantially pre-actuated position relative to the conductive pattern.

Furthermore, the control device may further comprise a secondary actuator adapted to transmit a secondary fluid actuation signal to the fluid delivery system, and the method may further comprise actuating the secondary actuator to transmit the secondary fluid actuation signal.

Further details and advantages of the present invention will become clear when reading the following detailed description in conjunction with the accompanying drawings, wherein like reference numerals represent like elements throughout.

DESCRIPTION OF THE PREFERRED EMBODIMENTS

Figure 1:
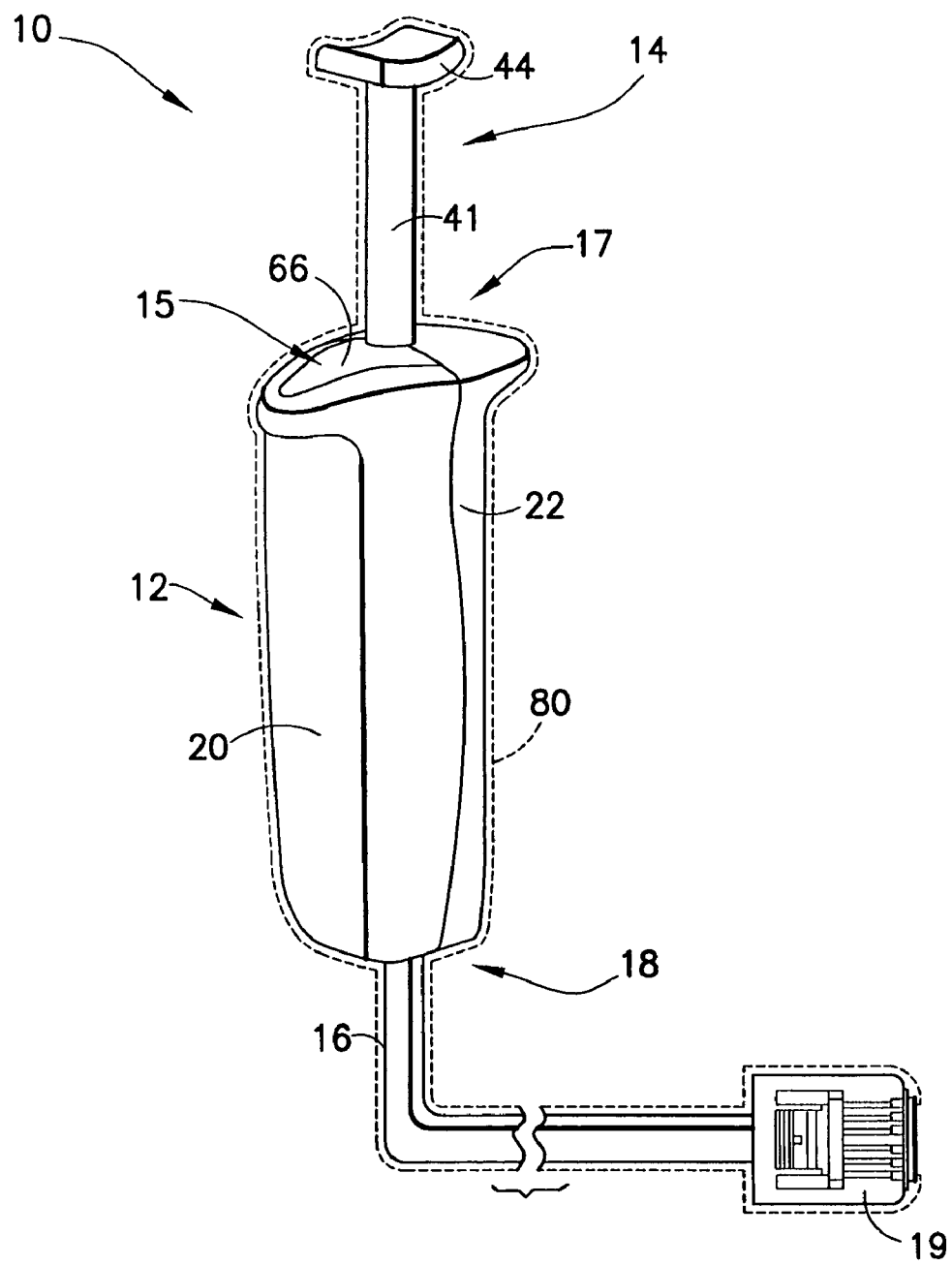
FIG. 1 is perspective view of a control device in accordance with the present invention.

For purposes of the description hereinafter, spatial or directional terms, such as "top", "bottom", "upper", "lower", "left", "right", "above", "below", and like terms, shall relate to the invention, as it is oriented in the drawing figures. However, it is to be understood that the invention may assume various alternative variations, except where expressly specified to the contrary. It is also to be understood that the specific apparatus illustrated in the attached drawings, and described in the following specification, are simply exemplary embodiments of the invention. Hence, specific dimensions and other physical characteristics related to the embodiments disclosed herein are not to be considered limiting.

Figure 2:
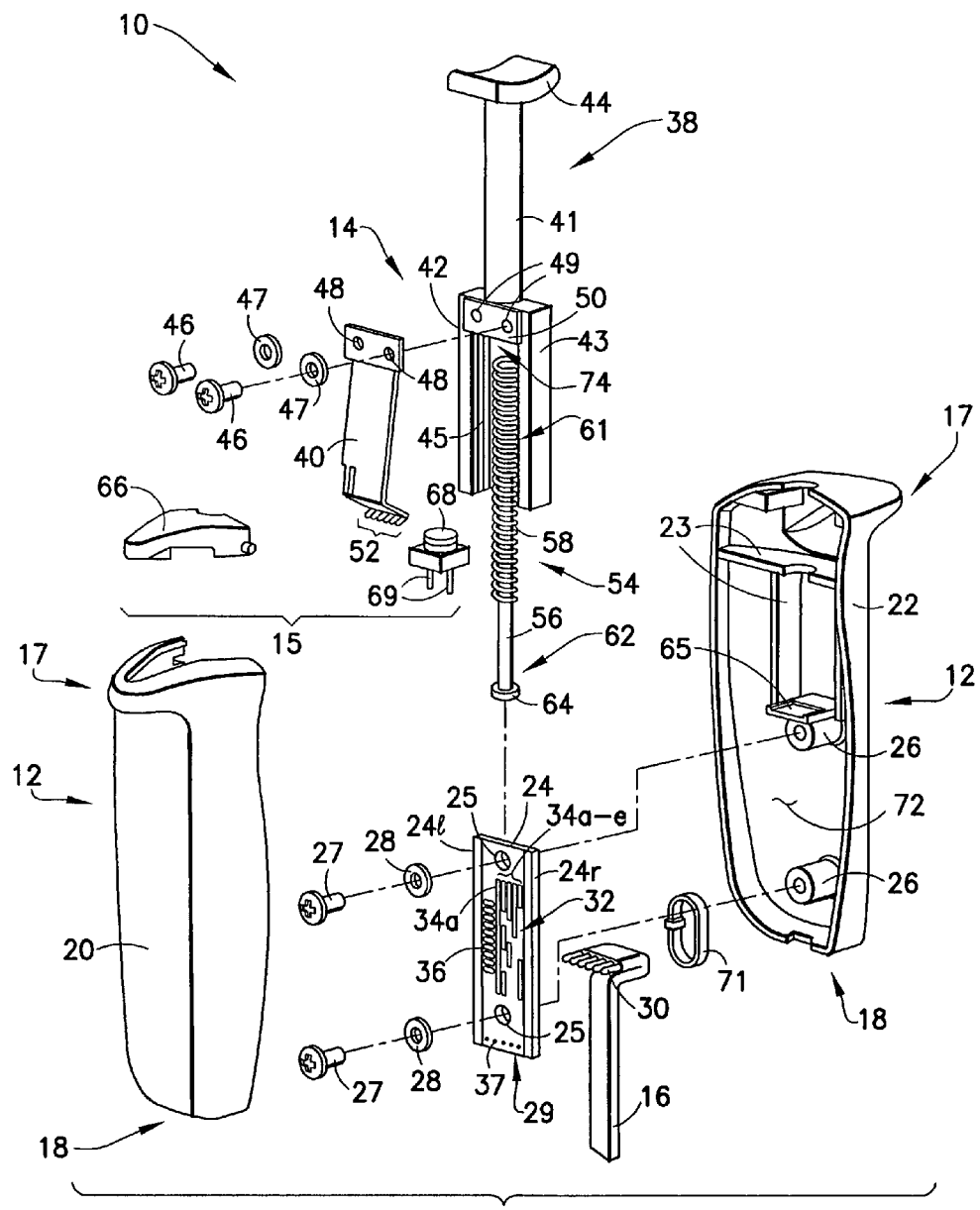
FIG. 2 is an exploded perspective view of the control device of FIG. 1.

A control device 10 according to the present invention is illustrated in FIGS. 1 and 2. The control device 10 is preferably configured to be hand-held, and will be referred to herein as "hand controller 10". However, this form of the control device 10 is merely exemplary, and the hand controller 10 may be provided as a foot-controller or a robotic actuated device as examples, or simply as an electronic console with one or more actuating devices, such as buttons, joysticks, and like elements.

Figure 4:
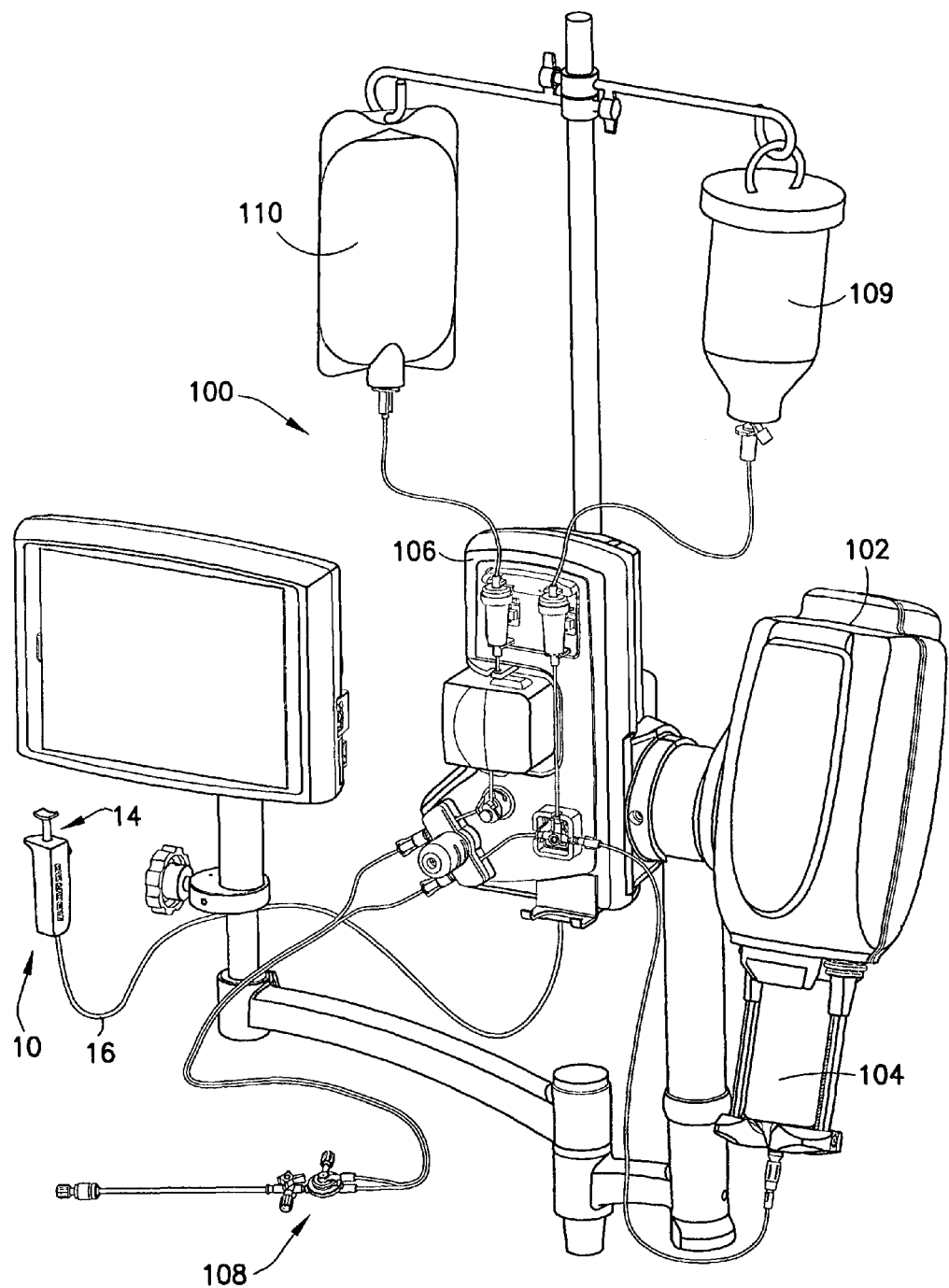
FIG. 4 is a perspective view of a fluid delivery system incorporating the control device of FIGS. 1 and 2.

The hand controller 10 is intended for use with an automatic fluid injection or delivery system 100, such as that generally illustrated in FIG. 4 discussed herein. The fluid delivery system 100 is used to deliver fluids to a patient during a medical injection procedure. For example, the fluid delivery system 100 may be used during an angiographic procedure to inject contrast media and common flushing agents, such as saline, into the body of a patient. An example of such a fluid injection or delivery system is disclosed in U.S. patent application Ser. No. 09/982,518, filed on Oct. 18, 2001, assigned to the assignee of the present application, the disclosure of which is incorporated herein by reference in its entirety. An additional example is disclosed in U.S. patent application Ser. No. 10/825,866, filed on Apr. 16, 2004, and entitled "Fluid Delivery System, Fluid Control Device, and Methods Associated with the Fluid Delivery System and Fluid Control Device", the disclosure of which is incorporated herein by reference in its entirety. The hand controller 10 is generally adapted to interface with one or more components of the fluid delivery system 100 to control the flow rates of the fluids, particularly contrast media in the case of angiographic procedures, to be delivered to the patient.

The hand controller 10 is generally adapted for electrical connection with the fluid delivery system 100, and controls the fluid delivery system 100 once the fluid delivery system 100 is appropriately programmed to accept input commands from the hand controller 10. More particularly, the hand controller 10 is adapted to digitally interface with the fluid delivery system 100 once associated therewith to deliver input commands to the fluid delivery system 100.

The hand controller 10 is further generally adapted to receive discrete physical inputs from a user or operator, select a predetermined digital value associated with each discrete physical input, and transmit the selected digital value to the fluid delivery system 100. The predetermined digital values or commands transmitted to the fluid delivery system 100 are converted into specific or discrete flow rate outputs from the fluid delivery system 100, which are delivered to the patient. Preferably, the digital values are proportional, for example, linearly proportional, to the user's physical inputs. The patient may be connected to the fluid delivery system 100 by means customary in the medical field, such as with a catheter.

With general reference to FIG. 1, the visible components of the hand controller 10 generally include a housing 12, an actuator 14 associated with the housing 12, a secondary actuator 15 also associated with the housing 12, and a cable 16 extending from the housing 12. The placement of these and any other components of the hand controller 10 are with reference to a first embodiment of the present invention, and should not be construed as limiting the present invention.

Generally, the actuator 14 and the secondary actuator 15 are disposed at a top end 17 of the housing 12, and the cable 16 extends from a bottom end 18 of the housing 12. The housing 12 may have an ergonomic shape, so that the hand controller 10 may be comfortably held in either the left or right hand by an operator, and to allow for single-handed operation thereof, as generally disclosed in U.S. patent application Ser. No. 10/237,139, filed on Sep. 6, 2002, assigned to the same assignee as the present application, the disclosure of which is incorporated herein in its entirety.

The housing 12 is preferably formed of plastic material, such as a suitable medical-grade plastic material. Inexpensive materials may be used for the housing 12 and the other components of the hand controller 10 to be discussed herein, so that the hand controller 10 may be a disposable item, disposed of, for example, after a preset number of procedures are conducted using the fluid delivery system 100. The housing 12 is formed to enclose and support the internal components of the hand controller 10 to be discussed herein. The hand controller 10 weighs in the range of about 0.25 to 1 pound, so that the hand controller 10 may be comfortably manipulated by an operator for extended periods of time without fatigue.

The cable 16 is generally adapted to transmit input commands in the form of digital values from the hand controller 10 to the fluid delivery system 100. The cable 16 may be any suitable type of cable adapted to digitally transfer the digital values to the fluid delivery system 100. For example, the cable 16 may be any suitable multiple-strand wiring cable, such as 6-pin phone cable. The cable 16 terminates in a connector 19, which is adapted to operatively and removably associate the hand controller 10 with the fluid delivery system 100. The connector 19 may be, for example, an RJ11 connector with 6 contacts, which allows the end of the cable 16 distal or remote from the hand controller 10 to have a positive locking electrical connection with a component of the fluid delivery system 100.

With reference to FIGS. 1 and 2, the internal components of the hand controller 10 will now be discussed. The housing 12 includes at least a first portion and a second portion, such as a left side or portion 20 and a right side or portion 22, respectively. However, the housing 12 may include any number of pieces or components and is generally intended to be a multi-piece structure. The left and right portions 20, 22 may include one or more internal rib structures 23 that provide structural support to the left and right portions 20, 22, and support locations for supporting various internal components of the hand controller 10, as discussed herein. Since the hand controller 10 may be provided as a disposable device, as indicated previously, the left and right portions 20, 22 may be permanently secured together with an adhesive bond or a permanent mechanical seal once the internal components of the hand controller 10 are assembled in place within the housing 12. Alternatively, the left and right portions 20, 22 may be removably secured together by conventional mechanical fasteners (not shown). The left and right portions 20, 22 are formed of plastic material, for example, a suitable medical-grade plastic material. Any inexpensive plastic or non-plastic material may be used for the left and right portions 20, 22, further facilitating the disposability of the hand controller 10.

The hand controller 10 further includes, internal to the housing 12, an electronic substrate 24, generally used to store the digital values to be transmitted via the cable 16 to the fluid delivery system 100. The electronic substrate 24 may be a conventional printed circuit board, and is generally a rectangular structure that defines opposing top and bottom holes 25. The electronic substrate 24 is secured to bosses 26 integrally formed with the right portion 22 of the housing 12 with conventional mechanical fasteners, such as screws 27 and washers 28. The body of the electronic substrate 24 defines one or more wire holes 29 for receiving one or more corresponding wires 30 of the cable 16 therein. The connection of the wires 30 with the wire holes 29 provides electrical connection and electronic data communication between the electronic substrate 24 and the fluid delivery system 100, once the connector 19 at the end of the cable 16 is connected to a component of the fluid delivery system 100. The electronic substrate 24 includes at least an equal number of wire holes 29 to the number of wires 30 in the cable 16.

Additionally, the electronic substrate 24 generally includes an electrical contact arrangement or conductive pattern 32 thereon. The conductive pattern 32 generally stores the digital values to be transmitted to the fluid delivery system 100. The digital values are in the form of binary values that generally correspond to specific or discrete flow rates to be delivered by the fluid delivery system 100 when the hand controller 10 is actuated, as discussed herein.

Generally, the conductive pattern 32, also referred to as a bit map herein, includes a plurality of columns, such as columns 34a-e, wherein each of the columns 34a-e includes at least one electrical contact and an adjoining space. Column 34a is a continual electrical ground contact and has no spaces. Thus, each of the columns 34b-e includes a combination of electrical contacts and spaces representing bit values, (i.e., 1 or 0). For example, from a top to bottom orientation in FIG. 2, column 34b includes an electrical contact, followed by a space, then followed by another electrical contact, which is then followed by yet another space, and finally, another electrical contact occupies the bottom of column 34b. In contrast, column 34d, for example, includes a single electrical contact that is followed by a single space. As shown in FIG. 2, each electrical contact and space in each of the columns 34b-e may be of various lengths.

A collinear horizontal grouping (i.e., row) of the electrical contacts and spaces includes the combination of either an electrical contact or a space from one or more of the columns 34b-e and electrical ground column 34a, with another electrical contact or space from another of the columns 34b-e. Thus, the conductive pattern 32 is generally divided into a plurality of collinear groupings (i.e., rows) of electrical contacts and spaces or bit values. The bit values for each of the columns 34l b-e defines a specific "preprogrammed" digital or binary value that is to be transmitted to the fluid control module 100 when operatively accessed by the actuator 14. Each collinear grouping (i.e., row) corresponds to a predetermined gray code (i.e., a series of bit values). The predetermined or preprogrammed digital or binary values are preferably linearly arranged within the conductive pattern 32 and represent corresponding discrete flow rates to be delivered from the fluid delivery system 100. More specifically, the predetermined or preprogrammed digital or binary values within the conductive pattern 32 (i.e., collinear rows taken from top to bottom) preferably correspond to incrementally increasing discrete fluid flow rates to be delivered from the fluid delivery system 100 when the actuator 14 is actuated, for example by the operator of the hand controller 10 moving the actuator 14 relative to the housing 12 as discussed herein. The gray code associated with the conductive pattern 32, as it relates to the delivery of flow rates from the fluid delivery system 100, may be generally as follows in Table 1:

TABLE 1

Gray Code & Flow Rate Assignment

| Gray Code | | | | Flow |
|---|---|---|---|---|
| Bit 3 | Bit 2 | Bit 1 | Bit 0 | Rate |
| 0 | 0 | 0 | 0 | 0% |
| 0 | 0 | 0 | 1 | 10% |
| 1 | 0 | 0 | 1 | 20% |
| 1 | 1 | 0 | 1 | 30% |
| 0 | 1 | 0 | 1 | 40% |
| 0 | 1 | 1 | 1 | 50% |
| 0 | 0 | 1 | 1 | 60% |
| 1 | 0 | 1 | 1 | 70% |
| 1 | 0 | 1 | 0 | 80% |
| 1 | 1 | 1 | 0 | 90% |
| 0 | 1 | 1 | 0 | 100% |

0 = corresponding bit connected to ground.
1 = corresponding bit open circuit.

The fluid delivery system 100 may utilize the foregoing gray code and the predetermined digital or binary values associated therewith to incrementally control the flow rate of the injection fluid (i.e., contrast media) in relation to a preprogrammed rate, such as 10 mL/s. For example, the predetermined digital or binary values may correspond to a predetermined volume per time rate, such as from 0 mL/s to the 10 mL/s rate, or a predetermined percentage rate of the preprogrammed rate, such as 0% to 100% of the 10 mL/s rate.

As is known in the art, gray code does not necessarily have a subsequent increasing binary value incremented by a bit value in the proper mathematically logical progression. Therefore, each subsequent collinear grouping (i.e., row) of the conductive pattern 32 does not need to conform to standard increasing binary value representation. For example, a flow rate of 0% may be represented by a collinear grouping (i.e., row) of four (4) electrical contacts (i.e., 0000) at the top of the conductive pattern 32. Immediately below this collinear grouping (i.e., row), the subsequent collinear grouping (i.e., row) may have three electrical contacts followed by a single space (i.e., 0001), which may correspond to a flow rate of 10%. The next collinear grouping (i.e., row), corresponding to a flow rate of 20%, may have a space followed by two electrical contacts, followed by another space (i.e., 1001). As the foregoing illustrates, the collinear groupings (i.e., rows) from the top to the bottom of the conductive pattern 32 do not necessarily correspond to standard increasing binary value representation, which would normally yield 0010 as the subsequent binary value for the 20% flow rate as an example.

In the present embodiment, the conductive pattern 32 includes eleven (11) collinear groupings (i.e., rows) to represent flow rates ranging from 0% to 100%. The first collinear grouping (i.e., digital or binary value) corresponds to no flow rate and the last collinear grouping (i.e., the 11$^{th}$ row) corresponds to 100% or maximum flow rate, which may be the maximum flow rate possible from the fluid delivery system 100 or a preprogrammed maximum flow rate preprogrammed into or permitted by the fluid delivery system 100. The respective digital or binary values programmed in the conductive pattern 32 are accessed by the actuator 14, the details of which are discussed herein. Generally, the actuator 14 is movably associated with the housing 12, such that movement of the actuator 14 accesses the digital or binary values preprogrammed in the conductive pattern 32.

The electronic substrate 24 further includes sound producing structures 36 that are preferably adapted to indicate when movement of the actuator 14 has taken place. The sound producing structures 36 may be simple mechanical structures, such as ridges or grooves formed on the electronic substrate 24, that are engaged by the actuator 14 when the actuator 14 is moved relative to the housing 12. The sound producing structures 36 are generally disposed adjacent the conductive pattern 32, and may be arranged to correspond to the digital or binary values preprogrammed in the conductive pattern 32 (i.e., correspond to the collinear groupings).

Alternatively, the mechanical sound producing structures 36 may be replaced by an electronic sound producing device in generally the same location as the mechanical sound producing structures 36. The electronic sound producing device may be in the form of frequency modulators that correspond, respectively, to the preprogrammed digital or binary values in the conductive pattern 32. As indicated, the mechanical sound producing structures 36 or equivalent electronic sound producing device are configured to audibly indicate movement of the actuator 14. The electronic substrate 24 further includes a ground electrical contact 37 that is in electrical contact with a corresponding ground wire of the cable 16.

The actuator 14 generally includes an actuating member 38, generally in the form of a plunger, that is movably associated with the housing 12, and a contact 40 that is generally adapted to operatively associate with the conductive pattern 32. The body of the actuating member 38 is formed with a rod portion 41 and left and right depending slide rails 42, 43. The end of the rod portion 41 includes a finger pad 44 for the operator of the hand controller 10 to place his or finger, thumb or palm (i.e., two fingers under flange portion of left and right portions 20, 22) to actuate the actuator 14. The left and right slide rails 42, 43 are sufficiently spaced apart to slidably accommodate the electronic substrate 24 therebetween. In particular, the left and right slide rails 42, 43 each define a guide track 45 for slidably receiving opposing lateral sides 24l, 24r of the electronic substrate 24, which enables the actuating member 38 to move up and down relative to the electronic substrate 24. The opposing guide tracks 45 defined by the respective left and right slide rails 42, 43 preferably extend the length of the left and right slide rails 42, 43.

The contact 40 is secured to the actuating member 38 by mechanical fasteners, such as screws 46 and cooperating washers 47. The screws 46 cooperate with holes 48 defined in the contact 40 and, further, may cooperate in a friction fit manner with corresponding holes 49 defined in an attachment plate or flange 50 connected to the actuating member 38, and generally extending between the left and right slide rails 42, 43. The contact 40 further includes a plurality of contact fingers 52 for contacting the conductive pattern 32 on the electronic substrate 24. The contact fingers 52 are adapted to contact the preprogrammed digital or binary values (i.e., collinear groupings) on the electronic substrate 24. Generally, the actuator 14 accesses the preprogrammed digital or binary values when an operator of the hand controller 10 engages and depresses the finger pad 44 associated with the rod portion 41, which causes the actuating member 38 to depress into the housing 12. The contact 40 of the actuator 14 will progress sequentially from the first discrete digital or binary value (i.e., collinear grouping 1) to subsequent discrete digital or binary values (i.e. collinear groupings 2-11) as the operator presses downward on the finger pad 44. The contact fingers 52 establish the electrical connection with the respective digital or binary values, which are transmitted to the fluid delivery system 100 via the cable 16. More specifically, the finger contacts 52 may contact either an electrical contact or a space in each of the columns 34b-e in the conductive pattern 32.

A biasing assembly 54 is associated with the actuator 14, and is disposed within the housing 12. The biasing assembly 54 is generally adapted to bias the actuator 14 against movement relative to the housing 12. The biasing assembly 54 is further adapted to provide increasing tactile resistance to the operator of the hand controller 10 the farther the actuating member 38 is moved (i.e., depressed into the housing 12). The biasing assembly 54 generally biases or tensions the rod portion 41 upward away from the electronic substrate 24.

The biasing assembly 54 generally includes a mandrel 56 associated with a compression spring 58. However, it will be apparent that suitable mechanically equivalent structures may be used in place of the mandrel 56 and compression spring 58 arrangement shown in FIG. 2, and discussed herein. The mandrel 56 generally has a first end 61 associated with the spring 58 and a second end 62 formed with an abutment flange 64. The abutment flange 64 is generally adapted to engage a corresponding surface or structure in the right portion 22 of the housing 12, which will allow the actuating member 38 to compress the spring 58 as the actuating member 38 is depressed into the housing 12 by the operator of the hand controller 10. For example, as shown in FIG. 2, one of the ribs 23 in the right portion 22 of the housing 12 may be formed with an engagement ledge 65 against which the abutment flange 64 contacts or rests to allow the actuating member 38 to compress the spring 58 as the actuating member 38 is depressed into the housing 12. The engagement ledge 65 may be recessed as illustrated in FIG. 2 to permit a mating engagement with the abutment flange 64.

The spring 58 is preferably configured such that the farther the actuating member 38 is depressed into the housing 12, the greater biasing force the operator of the hand controller 10 will experience. The first end 61 of the mandrel 56 is associated with the spring 58 and preferably acts as a spring-guide to prevent buckling of the spring 58 when the actuating member 38 is depressed.

The secondary actuator 15 is positioned generally adjacent the actuator 14, and is generally adapted to provide an actuation signal to the fluid delivery system 100 to cause the fluid delivery system 100 to deliver a secondary injection fluid to the patient. Such a secondary fluid may include saline supplied from a source of saline associated with the fluid delivery system 100. Saline is a common flushing agent used during medical injection procedures such as angiography. The secondary actuator 15 generally includes a control button 66 operatively associated with a switch 68 having leads 69, which are connected to the electronic substrate 24, for example by wires. The control button 66 is adapted for connection to the left portion 20 of the housing 12, such as by a pivotal connection therewith. The control button 66 is further generally adapted to contact or engage with the switch 68, when the control button 66 is depressed by the operator of the hand controller 10. Two switch wires (not shown) may connect the leads 69 to the wires holes 29 of the electronic substrate 24. Generally, when the operator of the hand controller 10 wants to initiate delivery of the secondary injection fluid, the operator depresses the control button 66 which engages the switch 68. The switch 68 then initiates the actuation signal, which is transmitted to the fluid delivery system 100 via the electronic substrate 24 and the cable 16.

Figure 3:
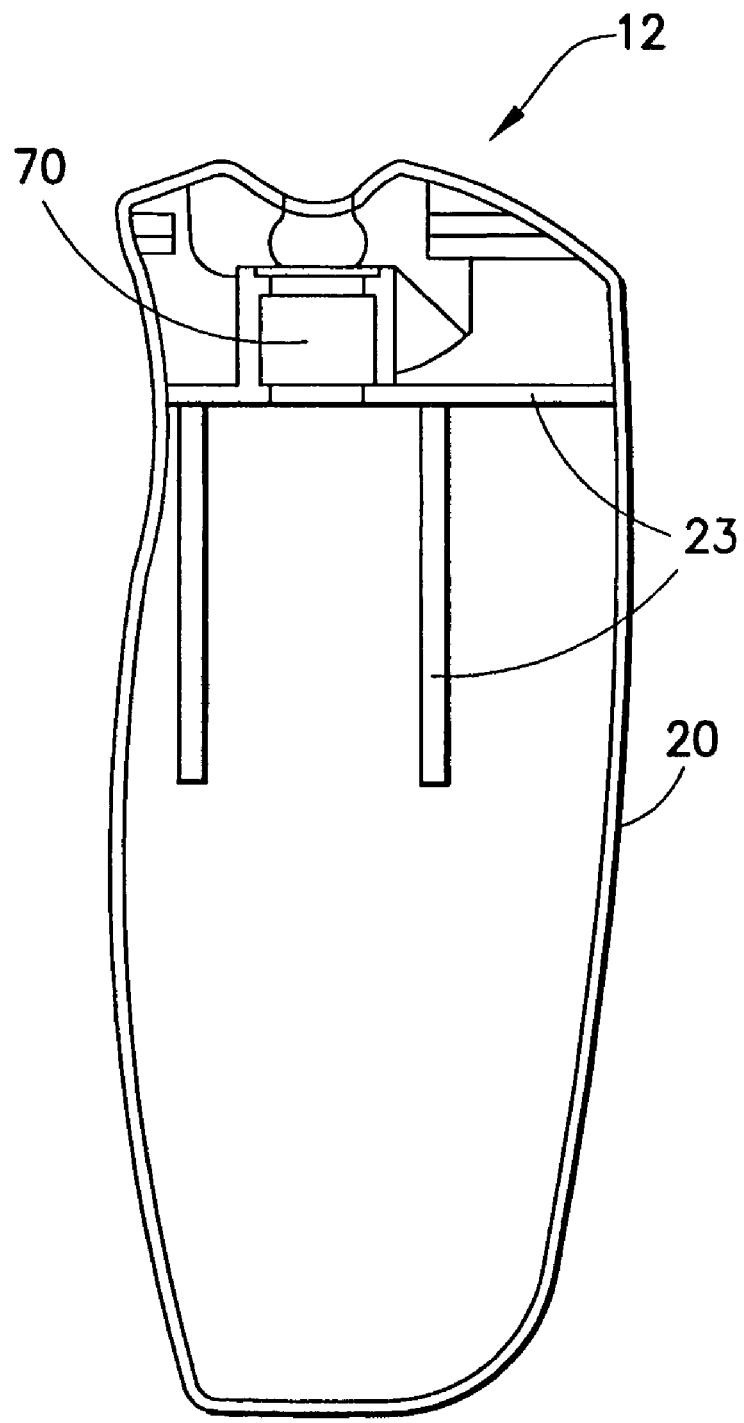
FIG. 3 is a side view of a housing of the control device of FIGS. 1 and 2.

With reference to FIGS. 2-4, one general method of assembling the hand controller 10 will now be discussed. Initially, the secondary actuator 15 may be assembled to the housing 12. This is accomplished by connecting the control button 66 with the left portion 20 of the housing 12 and positioning the switch 68 in a switch receiving pocket 70 defined by the left portion 20 of the housing 12. The switch receiving pocket 70 is defined by the internal rib structures 23 in the left portion 20 of the housing 12. The leads 69 from the switch 68 may then be associated with the electronic substrate 24 by suitable wiring.

Next, the wires 30 of the cable 16 may be secured in the corresponding wire holes 29 in the electronic substrate 24. A portion of the cable 16 will generally be retained within the right portion 22 of the housing 12, generally behind the electronic substrate 24. A cable tie 71 may be used to secure this portion of the cable 16 to provide strain relief. The tied portion of the cable 16 to be retained in the right portion 22 of the housing 12 is located in a cavity 72 defined by the right portion 22 of the housing 12. The electronic substrate 24 is used to secure the tied portion of the cable 16 when the electronic substrate 24 is secured to the right portion 22 of the housing 12 with the screws 27 and washers 28.

The actuator 14 may be pre-assembled prior to being received in the housing 12. The actuator 14 is generally assembled by connecting the contact 40 to the attachment plate 50 extending between the left and right slide rails 42, 43 with the screws 46 and cooperating washers 47. Thereafter, the biasing assembly 54 may be associated with the actuator 14. In particular, the compression spring 58 is placed about the mandrel 56 and the first end 61 of the mandrel 56 is located between the left and right slide rails 42, 43, so that the compression spring 58 is in position to operatively associate with the actuating member 38. The left and right slide rails 42, 43 generally define a receiving pocket 74 for the compression spring 58 and the first end 61 of the mandrel 56.

The actuator 14 and biasing assembly 54 may be placed in the right portion 22 of the housing 12 so that the abutment flange 64 on the mandrel 56 contacts the engagement ledge 65 defined by one of the internal rib structures 23 in the right portion 22. The actuator 14 is associated with the electronic substrate 24 as the actuator 14 is assembled in the right portion 22 of the housing 12 by receiving the opposing sides 24l, 24r thereof in the respective guide tracks 45 defined in the left and right slide rails 42, 43. The slidable engagement of the actuator 14 with the electronic substrate 24 allows the contact 40 of the actuator 14 to operatively associate with the conductive pattern 32. After applying a suitable adhesive to one or both of the left and right portions 20, 22 of the housing 12, the left and right portions 20, 22 may be aligned, closed upon each other, and bonded together with adhesive or mechanical fastening.

With reference to FIGS. 1-4, the operation of the hand controller 10 will now be discussed according to the above-discussed embodiment of the present invention. As indicated previously, the hand controller 10 is intended for use with the automatic fluid delivery system 100, which is generally illustrated in FIG. 4. The fluid delivery system 100 generally includes a powered injector 102 that is adapted to support and actuate a syringe 104 used to inject an injection fluid to a patient during a medical procedure, such as an angiographic procedure. The following operational discussion of the hand controller 10 will be with reference to an angiographic procedure involving the fluid delivery system 100, and how the hand controller 10 controls the delivery of the injection fluid from the fluid delivery system 100 to the patient. In typical angiographic procedures, the injection fluid is contrast media and such procedures typically further include saline as an additional or secondary injection fluid or flushing agent that is supplied to the patient.

The injector 102 is operatively associated with a fluid control module 106. The fluid control module 106 is generally adapted to support a fluid path set 108 that is generally adapted to fluidly connect the syringe 104 to a source of contrast media 109. The fluid path set 108 further connects the syringe 104 to a catheter (not shown) which is associated with the patient for supplying the contrast media to the patient. The fluid path set 108 is further connected to a source of saline 110 which is supplied to the patient via the same catheter as the contrast media. The contrast media flow from the syringe 104 and the saline flow to the patient is regulated by the fluid control module 106 which controls the various valves and flow regulating structures in the fluid path set 108 to regulate the delivery of contrast media and saline to the patient based on the digital values provided by the hand controller 10. The hand controller 10 is shown connected to the fluid control module 106 in FIG. 4. However, the hand controller 10 could also be connected directly with the injector 102. The injector 102 and the fluid control module 106 are preferably in electronic data communication, and the choice of associating the hand controller 10 with either the injector 102 or the fluid control module 106 primarily depends on the computer hardware and software associated with the injector 102 and the fluid control module 106. The injector 102 is generally used to supply the contrast media under pressure to the fluid path set 108 and, ultimately, the patient. The injector 102 is controlled by the hand controller 10 to supply the contrast media at discrete and preselected flow rates based on the physical inputs to the hand controller 10, as indicated previously.

To use the hand controller 10 with the fluid delivery system 100, the operator connects the cable 16 to the fluid control module 106 via the connector 19 at the end of the cable 16. The fluid control module 106 and injector 102 are programmed and set-up to receive input commands from the hand controller 10. Once the hand controller 10 is appropriately placed in electronic data communication with the fluid control module 106 and the injector 102 is appropriately primed with contrast media, the operator may actuate the hand controller 10. It is assumed for the sake of expedience in explaining operation of the hand controller 10 that all necessary steps have been accomplished to fill the syringe 104 with contrast media, and place the syringe 104 and the source of saline 110 in fluid communication with a patient via a catheter or other similar structure. Thus, the discussion herein regarding how the hand controller 10 controls the flow rate of contrast media and the supply of saline to the patient is with respect to an appropriately primed and programmed fluid delivery system 100.

To actuate the hand controller 10, the operator places his or her finger, thumb, or palm on the finger pad 44 disposed at the end of the rod portion 41 of the actuating member 38 of the actuator 14. As the actuating member 38 is depressed into the housing 12, the contact 40 moves from an initial, preactuated position generally associated with the first discrete digital or binary value in the conductive pattern 32 to another discrete digital or binary value, such as the second digital or binary value in the conductive pattern 32. The first discrete digital or binary position corresponds to a flow rate of 0% from the injector 102, and the second discrete digital or binary value corresponds, for example, to an incrementally increased flow rate of 10% flow rate from the injector 102. When the contact 40 of the actuator 14 is in the initial or preactuated position the digital or binary value of 0% flow rate associated therewith is continuously transmitted to the fluid control module 106 via the cable 16, and which interfaces electronically with the injector 102, for example by relaying the digital or binary value to the injector 102, which instructs the injector 102 not to actuate the syringe 104 and deliver fluid flow to the fluid path set 108. The biasing assembly 54 is associated with the actuator 14 as discussed in detail previously, and biases the actuating member 38 toward the initial or preactuated position, so that the initial or preactuated position of the actuating member 38 is the neutral or default position for the actuator 14, wherein no fluid flow is provided to the patient. Thus, if the operator for any reason discontinues pressure on the finger pad 44, the actuator 14 will automatically return to the neutral or default position where flow of contrast media is immediately discontinued.

When the contact 40 is in any other position with respect to the conductive pattern 32, the digital or binary value corresponding to that position is transmitted to the fluid control module 106 through the cable 16. It will generally be understood that as pressure is applied or released to the finger pad 44, the contact 40 will move freely up and down in contact with the conductive pattern 32, and output the various digital or binary values in the conductive pattern 32 to the fluid control module 106, which transmits the various digital or binary values as control signals to the injector 102. The injector 102 responds to the digital or binary values by supplying the contrast media at specific, discrete flow rates corresponding to a received digital or binary value until a new digital or binary values is received. Thus, the hand controller 10 generally takes an operator's physical inputs and selects or "looks up" a predetermined digital value associated with those inputs and digitally transmits the digital values to the injector 102, which responds to the digital values by delivering contrast media at pre-selected discrete flow rates corresponding to the digital values.

The hand controller 10 significantly improves over the prior art hand controllers discussed previously, because the prior art hand controllers are limited to continuously converting user physical (i.e., analog) inputs to digital outputs, without any means or method of regulating or dampening the output from the injector. In practice, it is known that even experienced operators of angiographic injection apparatus may over-inject contrast media into a patient's body during such procedures. In contrast, the hand controller 10 of the present invention is adapted such that in which each position of the physical structure used to make inputs to the hand controller 10 (i.e., the actuator 14) the position directly corresponds to a discrete digital value with no analog to digital conversion required. As the operator makes physical inputs to the actuator 14, the injector 102 will respond with discrete, stepped changes in flow rate, which are more easily monitored and controlled by the operator than the continuously variable flow rates provided by the prior art, as shown and described, for example, in U.S. Pat. No. 6,221,045. The prior art hand control devices discussed previously can lead to large swings in flow rates delivered to the patient, and the possible over-delivery of contrast media.

At any time during the injection procedure, the operator may depress the secondary actuator 15 to deliver a saline flush to the patient. To initiate the saline flush, the control button 66 is depressed, which initiates an actuation signal, for example, a saline start signal. Specifically, when the control button 66 is depressed, the control button 66 physically interacts with the switch 68, which initiates the actuation signal to the fluid control module 106. The actuation signal is transmitted via the electronic substrate 24 and the cable 16 to the fluid control module 106, which begins delivering saline from the source of saline 110 to the patient. If the primary actuator is actuated and the secondary actuator is then actuated or vice versa, the injector 102 will ignore the additional actuation. The secondary actuator 15 may be configured such that release of the control button 66 automatically ceases delivery of saline to the patient. Alternatively, the secondary actuator 15 may be configured such that a second depression of the control button 66 again will transmit a fluid stop signal to the fluid delivery system 100 which causes the fluid control module 106 to cease delivering saline.

It will generally be understood by those skilled in the art that the various signals transmitted by the hand controller 10 may be interpreted by the fluid control module 106 and/or injector 102 as either discrete flow or fixed flow signals, depending on how the fluid control module 106 and/or injector 102 are initially programmed. For example, the discrete flow signals may range from 0% to 100% of the preprogrammed flow rate. Alternatively, the fixed flow control signal may be 60% of the preprogrammed flow rate, such that when the actuating member 38 is in any position past the initial or preactuated position a fixed flow signal is automatically transmitted to the fluid delivery system 100.

In order to maintain sterility and prevent contamination, the hand controller 10 may utilize a sterile sheath 80 (See FIG. 1), which is configured as a generally form-fittingly envelope enclosing at least the housing 12 of the hand controller 10. The sterile sheath 80 may enclose the actuator 14 and cable 16 as shown in dotted lines in FIG. 1. The sterile sheath 80 may be transparent and is not intended to impair any operator functions of the hand controller 10. This optional sterile sheath 80 may be made of inexpensive material, preferably plastic, and disposed after each use of the hand controller 10, extending the usable "disposable" life of the hand controller 10.

The hand controller 10, upon actuation of the actuator 14, generally provides a variety of physical and/or auditory cues for relaying to the operator an indication that the hand controller 10 is operational. In particular, the hand controller 10 is adapted to indicate to the operator the distance of movement or length of travel of the actuating member 38 within the housing 12 when the finger pad 44 is depressed by the operator. The distance of movement of the actuating member 38 will intuitively tell the operator how fast the flow rate of contrast media will be and, consequently, how much contrast media is being delivered to the patient by the injector 102.

The distance of movement may be audibly ascertained by the engagement of the contact 40 with the sound producing structures 36 (i.e., ridges or grooves) on the electronic substrate 24, or by engagement of the contact 40 with an equivalent electronic sound producing on the electronic substrate 24. The engagement of the contact 40 with the sound producing structures 36 will make a clicking sound or other audible cue, and the engagement of the contact 40 with the electronic sound producing device will make an electronically generated sound or tone. In each case, the sound produced will give an indication as to the length or distance of movement of the actuating member 38 relative to the housing 12 and, hence, the corresponding flow rate delivered by the fluid delivery system 100.

Additionally, the sound producing structures 36 are raised from or indented sufficiently into the electronic substrate 24 such that the engagement of the contact 40 with the sound producing structures 36 provides the operator with tactile feedback indicating the length, distance or progression of movement of the actuating member 38 relative to the housing 12 (i.e., depression of the actuating member 38 in the housing 12). As generally indicated, the producing structures 36 may be formed as grooves, recesses, or indentations in the electronic substrate 24. Thus, the operator will experience tactile feedback that corresponds to the flow rate that will be delivered by the fluid delivery system 100 due to the engagement of the contact 40 with the sound producing structures 36.

Further, the biasing assembly 54 associated with the actuator 14 will provide immediate tactile feedback in the form of increasing resistive pressure as the actuating member 38 is depressed into the housing 12. Thus, the further the actuating member 38 is depressed into the housing 12, the more resistive force the operator will feel. The increasing resistance will provide immediate physical feedback that flow rate is increasing in the fluid path set 108 associated with the patient. The increasing resistance intuitively tells the operator that flow rate is increasing.

An alternative, second embodiment of the hand controller 10a is shown in FIGS. 5-9. The hand controller 10a is functionally identical to the foregoing embodiment of the hand controller 10. The housing 12a of the hand controller 10a has the same external appearance as the housing 12 of the foregoing embodiment of the hand controller 10, and includes left and right sides or portions 20a, 22a. The housing 12a is constructed of similar materials as the housing 12 in the previous embodiment. When the left and right portions 20a, 22a are joined to enclose the internal components of the hand controller 10a, the visible components of the hand controller 10a, including the actuating member 38a, finger pad 44a, control button 66a, and cable 16a, have generally the same external appearance as the forgoing embodiment of the hand controller 10. The internal components of the hand controller 10a have a slightly different configuration and arrangement from the first embodiment of the hand controller 10, and these differences will now be discussed with reference generally to FIGS. 5-9.

Initially, it is noted that the cable 16a used in the hand controller 10a is identical to the cable 16 discussed previously. The left and right portions 20a, 22a also include one or more internal rib structures 23a that provide structural support to the left and right portions 20a, 22a, and support locations for supporting various internal components of the hand controller 10a. As with the previous embodiment, the rib structures 23a are generally adapted to support the internal components of the of the hand controller 10a in the right portion 22a of the housing 12a. However, it will apparent when comparing FIGS. 2 and 5 that the arrangement of the rib structures 23a is formed slightly differently from the rib structures 23 discussed previously. In both cases, however, the rib structures 23, 23a in the right portion 22, 22a are generally adapted to support the internal components of the hand controller 10a, as indicated.

The right side or portion 22a of the housing 12a includes posts 204 in place of bosses 26. The posts 204 are adapted to mate or engage corresponding receptacles 206 formed internally in the left portion 20a of the housing 12a. The connection between the posts 204 and receptacles may be a compression friction fit. Thus, the left and right portions 20a, 22a may be permanently secured together via a compression fit between the posts 204 and receptacles 206, once the internal components of the hand controller 10a have been assembled in place within the housing 12a.

The electronic substrate 24a of the hand controller 10a is analogous in construction and operation to the electronic substrate 24 of the first embodiment of the hand controller 10. Thus, the electronic substrate 24a includes the same conductive pattern 32a and wire holes 29a as found on the electronic substrate 24. However, unlike the previous electronic substrate 24, the current electronic substrate 24a lacks the sound producing structures 36. Additionally, the holes 25a defined in the electronic substrate 24a are now adapted to accept the posts 204 extending from the right portion 22a of the housing 12a to mount the electronic substrate 24a in position within the right portion 22a and within the housing 12a generally. The hand controller 10a also uses an analogous electrical connection between the control button 66a and the electronic substrate 24a. As with the control button 66 discussed previously, the control button 66a is adapted for a pivotal association with the housing 12a. However, the control button 66a is now adapted for pivotal association with the right portion 22a of the housing 12a rather than the left portion 20a of the housing 12a, as was the case in the hand controller 10. The cable 16a is electrically connected to the electronic substrate 24a by associating the wires 30a of the cable 16a with the wire holes 29a in the electronic substrate 24a.

Figure 5:
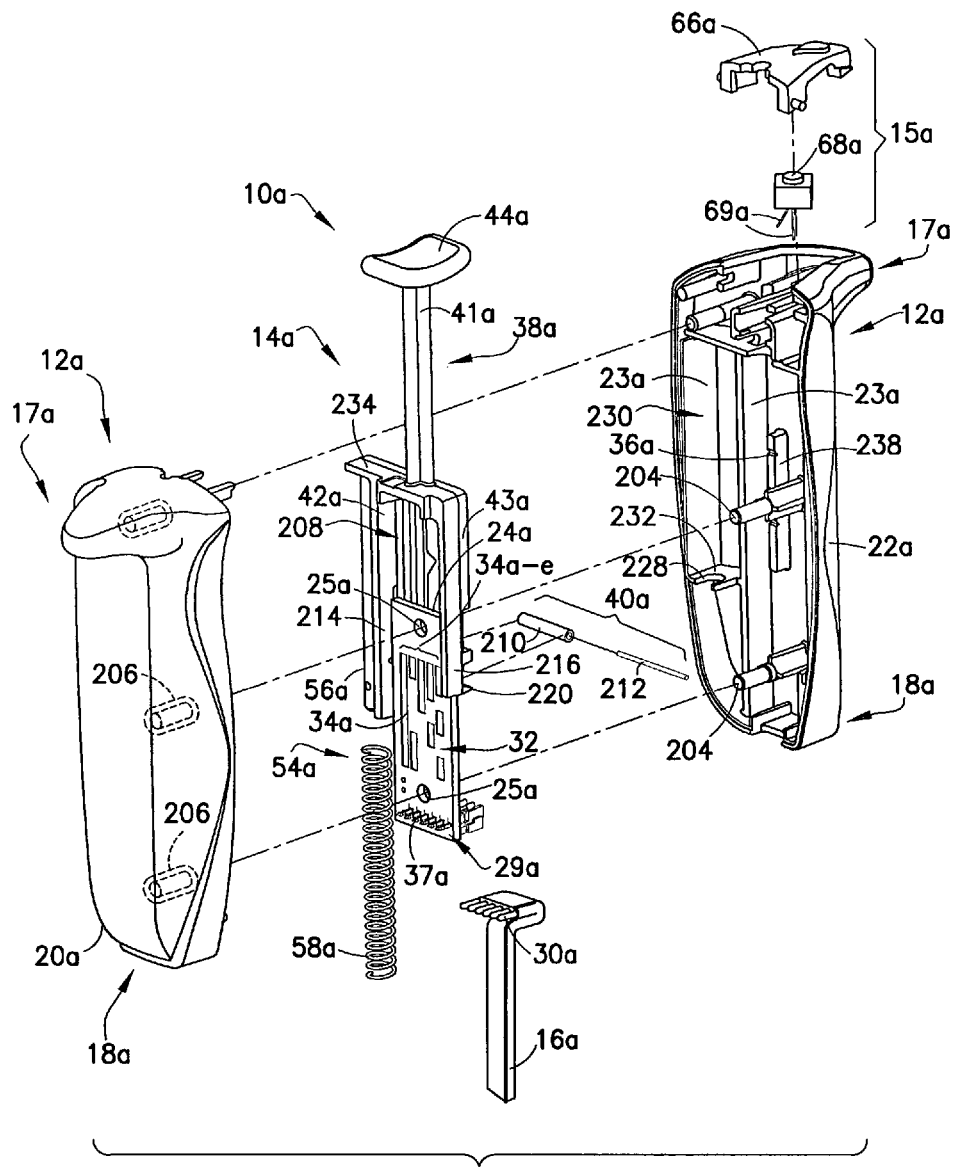
FIG. 5 is an exploded perspective view of an alternative embodiment of the control device.
Figure 6:
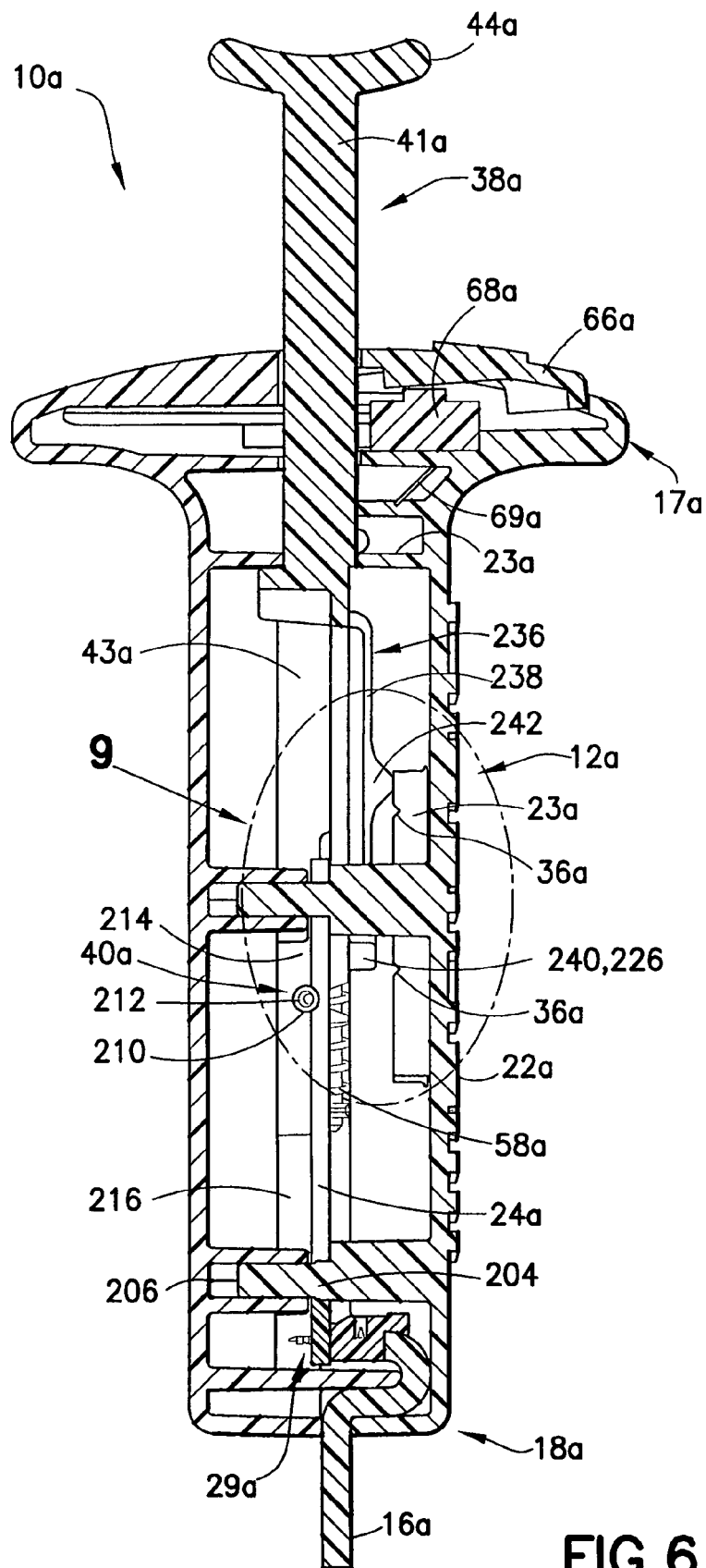
FIG. 6 is a left side and partial cross-sectional view of the assembled control device of FIG. 5.
Figure 7:
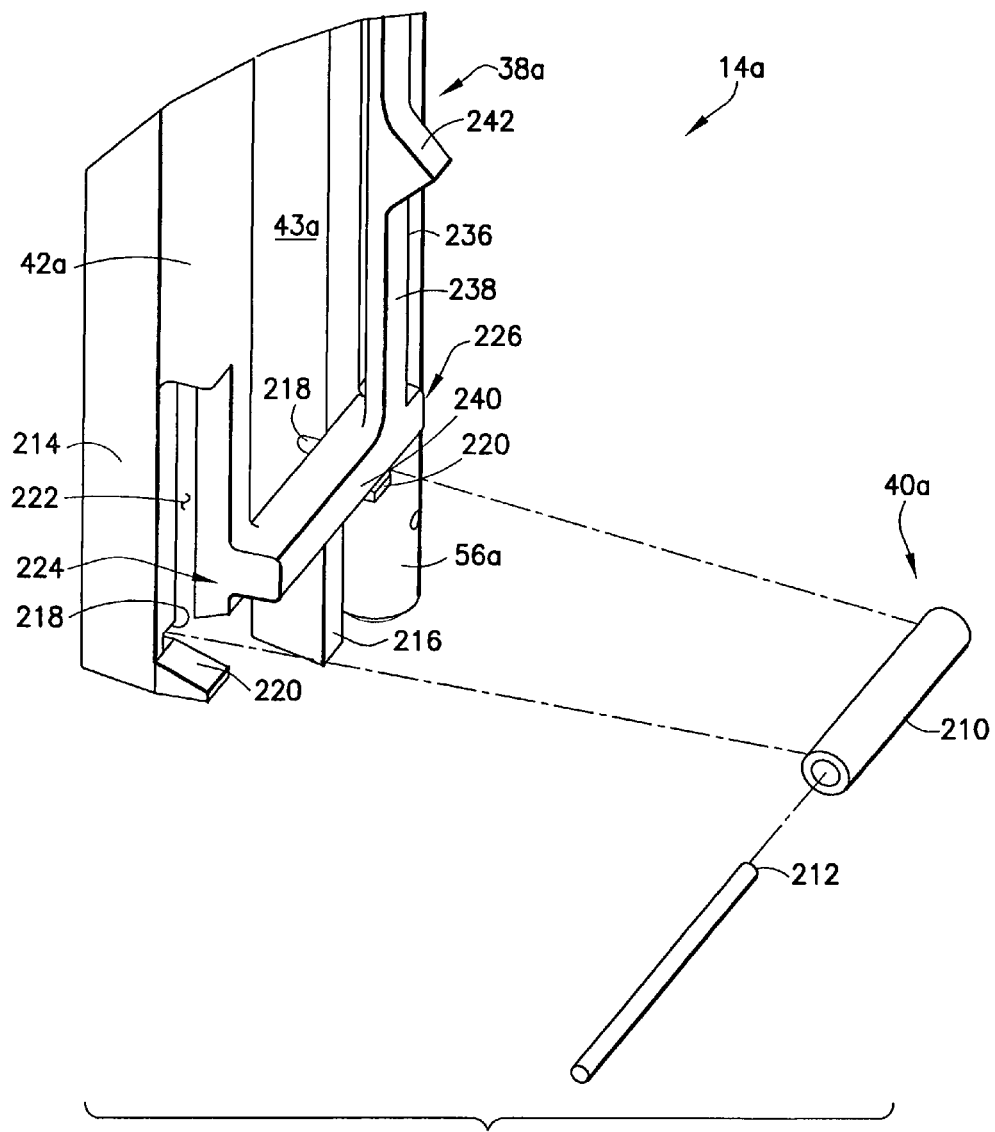
FIG. 7 is a perspective view of a bottom portion of an actuator of the control device of FIG. 5.
Figure 8:
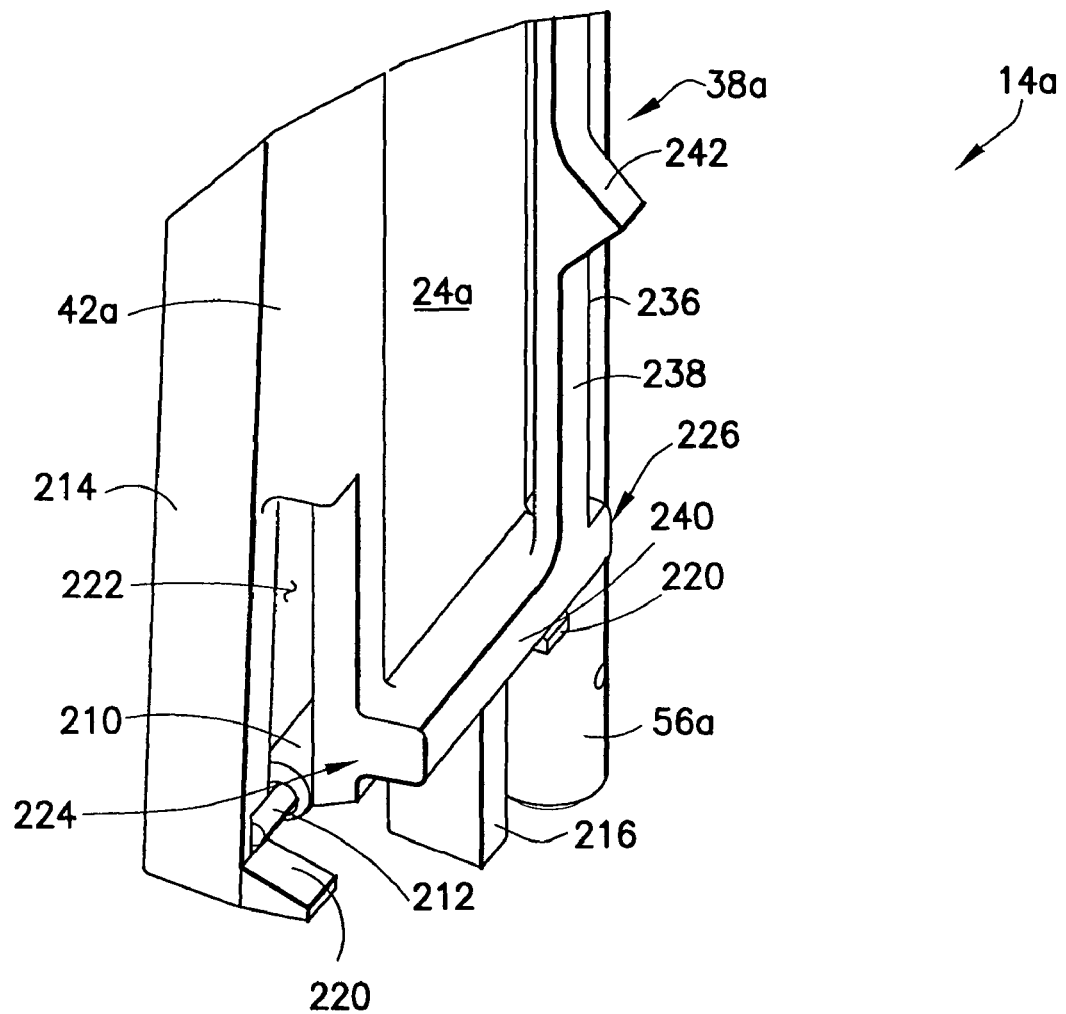
FIG. 8 is a perspective view of the bottom portion of the actuator of FIG. 5, showing a contact roller of the actuator.
Figure 9:
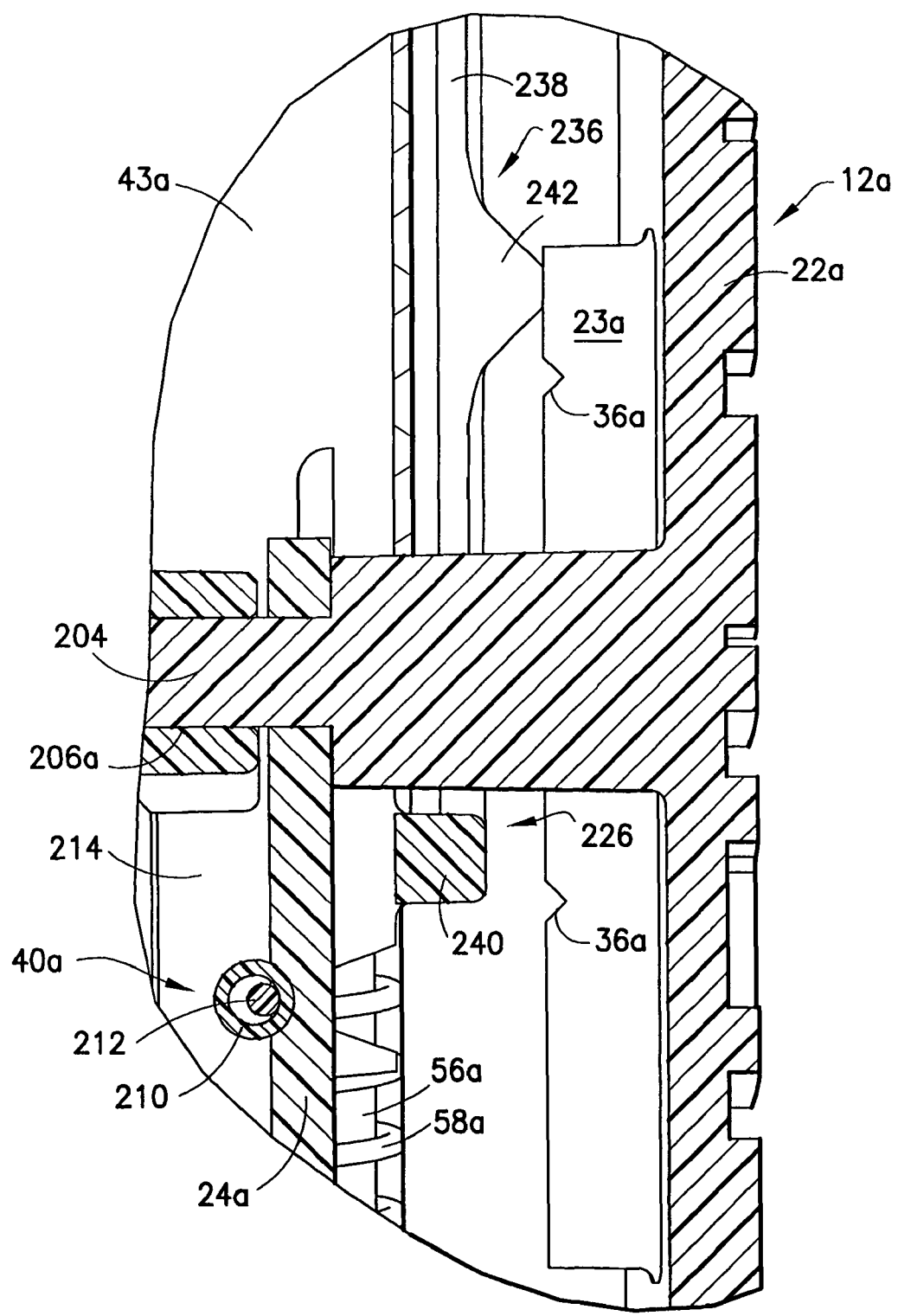
FIG. 9 is a detail and partial cross-sectional view of detail 9 in FIG. 6.

The sound producing structures 36a of the hand controller 10a are provided in a different location from the first embodiment of the hand controller 10. Specifically, the sound producing structures 36a are now provided on one of the rib structures 23a in the right portion 22a of the housing 12a. The sound producing structures 36a may again be formed as ridges or grooves. However, the sound producing structures 36a may further be formed as angled indents or recesses in the rib structure 23a as shown in FIGS. 5, 6, and 9. If the sound producing structures 36a are formed as ridges or similar raised structures, such raised structures may be formed as angled or pointed tabs on the rib structure 23a. Additionally, the "raised" version of the sound producing structures 36a may be formed integrally with the rib structure 23a, or provided as separate structures secured to the rib structure 23a. Additionally, the sound producing structures 36a may be provided in any convenient location within the housing 12a. For example, the sound producing structures 36a may be arranged within the same vertical plane and spaced in parallel relation to the electronic substrate 24a. As indicated previously, the sound producing structures 36a provide the user with an auditory and tactile indication of the actuation of the hand controller 10a. The sound producing structures 36a are physically engaged by a portion of the actuator 14a, as will be discussed further herein, to produce the auditory and tactile indications to the user. As further indicated previously, the sound producing structures 36a may be replaced by a generally equivalent electronic sound producing device.

The actuator 14a of the hand controller 10a has a similar overall external appearance to the actuator 14 discussed previously. However, the actuator 14a is configured to operatively associate with the conductive pattern 32 in a slightly different manner than the actuator 14 discussed previously. One difference between the actuator 14a and the actuator 14 discussed previously lies in the form of the contact 40a. An additional difference relates to the form and construction of the actuating member 38a of the actuator 14a, and how the actuating member 38a supports the contact 40a. A further difference relates to the way the actuator 14a interacts with the sound producing structures 36a now disposed in the right portion 22a of the housing 12a. A still further difference relates to the location and configuration of the biasing assembly 54a of the actuator 14a. Each of the foregoing differences and others will be discussed in detail herein.

Beginning with the actuating member 38a, the actuating member 38a exhibits the same general "plunger" form and operation as the actuating member 38 discussed previously. The left and right slide rails 42a, 43a of the actuating member 38a are spaced apart to accept the electronic substrate 24a therebetween. However, the slide rails 42a, 43a no longer define guide tracks 45 for slidably accepting the electronic substrate 24a. Accordingly, the side rails 42a, 43a will be referred to hereinafter simply as "rails 42a, 43a". The rails 42a, 43a define a generally rectangular-shaped receiving pocket 208 for accommodating the electronic substrate 24a. The rod portion 41a of the actuating member 38a is formed integrally with the rails 42a, 43a in a similar manner to the actuating member 38 discussed previously. Since the electronic substrate 24a is fixedly mounted on the posts 204 when the left and right portions 20a, 22a of the housing 12a are joined together, the receiving pocket 208 is sized sufficiently to allow the actuating member 38a to move up and down relative to the electronic substrate 24a (i.e., slidably along the electronic substrate 24a).

The actuating member 38a is generally configured to support an alternative embodiment or variation of the contact 40 discussed previously. The contact 40 described previously is formed generally as a plate-like structure or member and is secured to the actuating member 38 with mechanical fasteners 46, 47. The contact 40 included contact fingers 52 for interacting with the electronic substrate 24 and sound producing structures 36.

In the present embodiment, the actuating member 38a is also configured to support the contact 40a, but the contact 40a now is in the form of a contact roller and will be referred to hereinafter as "contact roller 40a". The contact roller 40a includes a roller 210 rotatably mounted on an axle 212. The axle 212 is in turn rotatably supported by the actuating member 38a. In the present embodiment, the actuating member 38a is specifically adapted to rotatably support the contact roller 40a. The roller 210 is constructed of resilient and conductive material, such as conductive rubber. For example, the roller 210 may be a silicone based extruded elastomer having a silver-copper blend filing. However, the roller 210 may be made of any suitable conductive material, such as metal and, in particular, aluminum.

To support the contact roller 40a, the rails 42a, 43a of the actuating member 38a include extended support members 214, 216 adapted to rotatably support the axle 212. The support members 214, 216 may be integral, extended portions of the respective rails 42a, 43a. The support members 214, 216 define opposing notches or recesses 218 for rotatably supporting the ends of the axle 212. The support members 214, 216 further include guide tabs or ramps 220 disposed immediately adjacent the notches 218 to guide entry of the ends of the axle 212 into the notches 218 when the actuator 14a is assembled.

The support members 214, 216 define longitudinal gaps 222 with distal ends 224, 226 of the rails 42a, 43a. The longitudinal gaps 222 allow the respective support members 214, 216 to flex relative to the distal ends 224, 226 of the rails 42a, 43a when the contact roller 40a is mounted to the support members 214, 216 and engaged with the electronic substrate 24a. When the actuator 14a is assembled and mounted in place between the left and right portions 20a, 22a of the housing 12a, the actuating member 38a including the rails 42a, 43a and support members 214, 216 are movable up and down within the housing 12a in the manner explained in detail previously in connection with the hand controller 10. However, due to the engagement of the roller 210 with the electronic substrate 24a in the present embodiment, the support members 214, 216 will be flexed outward (i.e., generally transversely) a small distance from the rails 42a, 43a and, more particularly, outward from the distal ends 224, 226 of the rails 42a, 43a. The "flexure" of the support members 214, 216 is caused by sizing the distance between the root of the notches 218 and the surface of the electronic substrate 24a slightly smaller than the diameter of the roller 210. As a result, when the axle 212 is mounted in the notches 218 and the electronic substrate 24a is fixed to the posts 204, the roller 210 through the axle 212 will cause the support members 214, 216 to flex or cantilever away from the distal ends 224, 226 of the rails 42a, 43a. This flexure applies a return or "back" pressure on the roller 210 through the axle 212. The back pressure on the roller 210 causes the resilient material of the roller 210 to deform and "mold" into engagement with the conductive pattern 32a on the electronic substrate 24a, resulting in a generally improved electrical contact between the contact roller 40a and conductive pattern 32a. The resiliency of the material forming the roller 210 and applied back pressure allows the roller 210 to accommodate height variances present in the electrical contacts or columns 34a-e forming the conductive pattern 32a. However, the back pressure is not significant enough to impede rotation of the roller 210 along the surface of the electronic substrate 24a.

The actuating member 38a and, by extension, the support members 214, 216 and rails 42a, 43a are made of a resiliently deformable or deflectable material such as plastic to allow for the flexure of the support members 214, 216. It will be generally understood that the back pressure or "flexure" force applied by the support members 214, 216 will be proportional to the flexibility of the material forming the actuating member 38a. The support members 214, 216 do not necessarily have to be formed integrally with the rails 42a, 43a and could be provided as separate elements that are secured to the rails 42a, 43a. Alternatively, since the support members 214, 216 are generally adapted to bias the roller 210 into engagement with the electronic substrate 24a, the support members 214, 216 could be replaced by a suitable mechanically equivalent biasing structure associated with the axle 212 and roller 210 to bias the roller 210 into engagement with the electronic substrate 24a. Such an arrangement could include one or more biasing elements, such as compression or leaf springs, associated with the axle 212 to bias the roller 210 into engagement with the electronic substrate 24a.

The contact roller 40a when biased into engagement with the electronic substrate 24a by the arrangement described hereinabove exerts a continuous and consistent pressure over the surface of the electronic substrate 24a and, specifically, the conductive pattern 32a. However, as indicated, the roller 210 is not impeded to a degree that would prevent the roller 210 from rotating on the axle 212 and rolling along the surface of the electronic substrate 24a based on inputs from the user or biasing assembly 54a to be discussed hereinbelow. As with the contact 40 discussed previously having contact fingers 52, the roller 210 of the contact 40a allows for selective shorting across the conductive pattern 32a to allow sequential access to the predetermined digital values in the conductive pattern 32a when the actuating member 38a is actuated by a user.

The biasing assembly 54a is provided in a different location from the biasing assembly 54 discussed previously, but includes the same general components as the earlier embodiment of the biasing assembly 54 and is functionally identical to the biasing assembly 54 discussed previously. The mandrel 56a is now formed integrally with the actuating member 38a. The mandrel 56a is located adjacent and generally parallel to the left rail 42a and is disposed substantially within the right portion 22a of the housing 12a when the hand controller 10a is assembled. However, the mandrel 56a may be associated with the actuating member 38a in any convenient location to allow for the biasing of the actuating member 38a to the neutral or no-flow position described previously in connection with the hand controller 10. The spring 58a is associated with the mandrel 56a in a similar manner to the mandrel 56 and spring 58 discussed previously. However, as will be clear when viewing FIG. 5, the mandrel 58a no longer engages a ledge formed on one of the rib structures 23a, but extends through a recess 228 defined in one of the rib structures 23a in the right portion 22a of the housing 12a. In particular, the rib structures 23a in the right portion 12a generally define an internal pocket 230 for receiving both the spring 58a and mandrel 56a. The bottom of the internal pocket 230 forms a ledge 232 for supporting one end of the spring 58a. The ledge 232 is similar in function to the ledge 65 described previously in connection with the hand controller 10. However, in the present embodiment, the spring 58a now acts between the ledge 232 and an upper cross member 234 of the actuating member 38a. Thus, when the mandrel 56a is moved downward in the internal pocket 230 as the actuating member 38a is depressed into the housing 12a by a user, the compression spring 58 is compressed within the internal pocket 230. The compression spring 58a provides a counteracting biasing force against the downward movement, and biases the actuating member 38a to the neutral or no-flow position discussed previously.

The actuating member 38a further includes an additional structure 236 for interacting with the sound producing structures 36a now provided on/in one of the rib structures 23a in the right portion 22a of the housing 12a. The "sound producing" structure 236 generally includes one longitudinal member 238 connected to the cross member 234 of the actuating member 38a and one transverse member 240 interconnecting the distal ends 224, 226 of the rails 42a, 43a. The transverse member 240 provides structural reinforcement to the distal ends 224, 226 of the rails 42a, 43a.

The longitudinal member 238 includes a raised tab or detent 242 that engages with the sound producing structures 36a. The tab 242 is angled or pointed to engage the raised, angled ridges or V-shaped indents or grooves forming the sound producing structures 36a. The raised ridges or V-shaped indents or grooves forming the sound producing structures 36a may be formed in a manner to generally correspond to the tab 242. The engagement of the tab 242 with the sound producing structures 36a will produce a distinct "clicking" sound as these elements engage one another. This engagement will also be tactilely apparent to the user of the hand controller 10a as the opposing tabs move over one another. Thus, the engagement of the tab 242 with the corresponding sound producing structures 36a provide both audible and tactile feedback to the user of the hand controller 10a during a fluid injection procedure. Other than the internal differences between the hand controller 10a discussed in the forgoing paragraphs, there is substantially no difference in operation between the two hand controllers 10, 10a.

While the present invention was described with reference to exemplary and alternative embodiments of the hand controller, those skilled in the art may make modifications and alterations to the present invention without departing from the scope and spirit of the invention. Accordingly, the foregoing detailed description is intended to be illustrative rather than restrictive. The invention is defined by the appended claims, and all changes to the invention that fall within the meaning and range of equivalency of the claims are to be embraced within their scope.

The invention claimed is:

1. A fluid delivery system for use in medical procedures, comprising:
 an injector for delivering an injection fluid to a patient; and
 a control device operatively associated with the injector for controlling flow rates of the injection fluid delivered to the patient, the control device comprising:
  a housing;
  an actuator movably associated with the housing, the actuator comprising an actuating member comprising a left rail and a right rail that cooperate to define a generally rectangular-shaped receiving pocket therebetween and a contact roller movably connected to the actuating member, the contact roller comprising a roller rotatably mounted on an axle that is rotatably supported by and disposed between the left and right rails of the actuating member, the roller being formed of an electrically conductive resilient material; and an electronic substrate mounted to the housing and adapted to be received within the generally rectangular-shaped receiving pocket defined by the left and right rails of the actuating member, the electronic substrate comprising a conductive pattern and the roller of the actuator being adapted to engage the conductive pattern when the actuating member of the actuator is actuated by a user;

wherein the conductive pattern comprises a plurality of predetermined digital values corresponding to discrete flow rates of the injection fluid to be delivered by the injector, such that when the actuating member of the actuator is actuated by the user and moved relative to the housing, the roller of the actuator engages with and sequentially accesses the digital values of the conductive pattern and transmits the digital values to the injector.

2. The fluid delivery system of claim 1, wherein the digital values are arranged such that the discrete flow rates are linearly proportional to distance of movement of the actuator.

3. The fluid delivery system of claim 1, wherein the digital values are arranged such that the discrete flow rates incrementally increase with distance of movement of the actuator.

4. The fluid delivery system of claim 3, wherein the digital values comprise at least a first digital value corresponding to no movement of the actuator and a 0% of discrete flow rate from the injector, and a last digital value corresponding to a maximum movement of the actuator and a 100% discrete flow rate from the injector.

5. The fluid delivery system of claim 1, wherein the roller is biased into engagement with the electronic substrate.

6. The fluid delivery system of claim 1, further comprising a biasing member associated with the actuating member for biasing the actuating member to a neutral position relative to the housing.

7. The fluid delivery system of claim 6, wherein the biasing member acts on the actuating member such that the user of the control device experiences increasing tactile resistance as the actuating member is moved relative to the housing.

8. The fluid delivery system of claim 1, wherein the actuator comprises a biasing member adapted to provide tactile resistance proportional to distance of movement of the actuator relative to the housing.

9. The fluid delivery system of claim 1, wherein one of the electronic substrate and the housing comprises sound producing structures positioned to be engaged by the actuator for audibly indicating movement of the actuator relative to the housing.

10. The fluid delivery system of claim 1, wherein the housing is configured to be hand-held.

11. The fluid delivery system of claim 1, wherein the control device further comprises a secondary actuator adapted to transmit a secondary fluid actuation signal upon actuation.

12. The fluid delivery system of claim 11, wherein the secondary actuator comprises a control button operatively associated with the electronic substrate for initiating the secondary fluid actuation signal.

13. A control device for controlling a fluid delivery system, comprising:
a hand-held housing;
an actuator movably associated with the housing, the actuator comprising an actuating member comprising a left rail and a right rail that cooperate to define a generally rectangular-shaped receiving pocket therebetween and a contact roller movably connected to the actuating member, the contact roller comprising a roller rotatably mounted on an axle that is rotatably supported by and disposed between the left and right rails of the actuating member, the roller being formed of an electrically conductive resilient material; and an electronic substrate mounted to the housing and adapted to be received within the generally rectangular-shaped receiving pocket defined by the left and right rails of the actuating member, the electronic substrate comprising a conductive pattern and the roller of the actuator being adapted to engage the conductive pattern when the actuating member of the actuator is actuated by a user, and wherein the conductive pattern comprises a plurality of predetermined digital values corresponding to discrete flow rates of injection fluid to be delivered by the fluid delivery system, such that when the actuating member of the actuator is actuated by the user and moved relative to the housing, the roller of the actuator engages with and sequentially accesses the digital values of the conductive pattern and transmits the digital values to the fluid delivery system.

14. The control device of claim 13, wherein the digital values are arranged such that the discrete flow rates are linearly proportional to distance of movement of the actuator.

15. The control device of claim 13, wherein the digital values are arranged such that the discrete flow rates incrementally increase with distance of movement of the actuator.

16. The control device of claim 15, wherein the digital values comprise at least a first digital value corresponding to no movement of the actuator and a 0% discrete flow rate from the fluid delivery, and a last digital value corresponding to a maximum movement of the actuator and a 100% discrete flow rate from the fluid delivery system.

17. The control device of claim 13, wherein the roller is biased into engagement with the electronic substrate.

18. The control device of claim 13, further comprising a biasing member associated with the actuating member for biasing the actuating member to a neutral position relative to the housing.

19. The control device of claim 18, wherein the biasing member acts on the actuating member such that the user of the control device experiences increasing tactile resistance as the actuating member is moved relative to the housing.

20. The control device of claim 13, wherein the actuator comprises a biasing member adapted to provide tactile resistance proportional to distance of movement of the actuator relative to the housing.

21. The control device of claim 13, wherein one of the electronic substrate and the housing comprises sound producing structures positioned to be engaged by the actuator for audibly indicating movement of the actuator relative to the housing.

22. The control device of claim 13, wherein the control device further comprises a secondary actuator adapted to transmit a secondary fluid actuation signal upon actuation.

23. A method of controlling a fluid delivery system comprising an injector for delivering an injection fluid to a patient, comprising:
operatively connecting a control device to the injector, the control device adapted to control discrete flow rates of the injection fluid to be delivered by the injector to the patient; and
actuating the control device to transmit one or more predetermined digital values to the injector to control the discrete flow rates of the injection fluid delivered by the injector;

wherein the control device comprises a hand-held housing, an actuator movably associated with the housing, the actuator comprising an actuating member comprising a left rail and a right rail that cooperate to define a generally rectangular-shaped receiving pocket therebetween and a contact roller movably connected to the actuating member, the contact roller comprising a roller rotatably mounted on an axle that is rotatably supported by and disposed between the left and right rails of the actuating member, the roller being formed of an electrically conductive resilient material, and an electronic substrate mounted to the housing and adapted to be received within the generally rectangular-shaped receiving pocket defined by the left and right rails of the actuating member, the electronic substrate comprising a conductive pattern and the roller of the actuator being adapted to engage the conductive pattern when the actuating member of the actuator is actuated by a user, and wherein the conductive pattern comprises a plurality of predetermined digital values corresponding to discrete flow rates of injection fluid to be delivered by the injector, such that when the actuating member of the actuator is actuated by the user and moved relative to the housing, the roller of the actuator engages with and sequentially accesses the digital values of the conductive pattern and transmits the digital values to the injector.

24. The method of claim 23, wherein the contact operatively contacts the conductive pattern by rolling along the surface of the conductive pattern.

25. The method of claim 23, further comprising audibly indicating movement of the actuator relative to the conductive pattern.

26. The method of claim 23, further comprising a biasing member associated with the actuator for biasing the actuator against movement relative to the conductive pattern, the method further comprising discontinuing actuation of the control device such that the biasing member returns the actuator to a substantially pre-actuated position relative to the conductive pattern.

27. The method of claim 23, wherein the control device further comprises a secondary actuator adapted to transmit a secondary fluid actuation signal to the fluid delivery system, and the method further comprises actuating the secondary actuator to transmit the secondary fluid actuation signal.

28. The fluid delivery system of claim 1, wherein the control device further comprises a cable extending from the housing to the injector, the cable being adapted to transmit the digital values accessed by the contact roller to the injector.

29. The fluid delivery system of claim 28, wherein the cable is removably connectable to the injector by means of a connector.

30. The fluid delivery system of claim 29, wherein the connector is adapted to provide a positive locking connection with the injector.

31. The fluid delivery system of claim 30 wherein the connector is an RJ11 connector with 6 contacts.

32. The fluid delivery system of claim 28 wherein the cable is a 6-pin phone cable.

33. The fluid delivery system of claim 1 wherein the actuating member comprises a rod portion having a pad on one end thereof for the user to place a finger, thumb or palm to actuate the actuator.

34. The method of claim 23, further comprising the step of disposing of the control device after a preset number of procedures have been conducted using the fluid delivery system.

35. The control device of claim 13, further comprising a cable extending from the housing to the fluid delivery system, the cable being adapted to transmit the digital values accessed by the contact roller to the fluid delivery system.

36. The control device of claim 35, wherein the cable is removably connectable to the fluid delivery system by means of a connector.

37. The control device of claim 36, wherein the connector is adapted to provide a positive locking connection with the fluid delivery system.

38. The control device of claim 37 wherein the connector is an RJ11 connector with 6 contacts.

39. The control device of claim 35 wherein the cable is a 6-pin phone cable.

* * * * *

UNITED STATES PATENT AND TRADEMARK OFFICE
CERTIFICATE OF CORRECTION

PATENT NO. : 7,879,008 B2  
APPLICATION NO. : 11/085616  
DATED : February 1, 2011  
INVENTOR(S) : Haury et al.

Page 1 of 1

It is certified that error appears in the above-identified patent and that said Letters Patent is hereby corrected as shown below:

In Column 8, Line 49, delete "34l b-3" and insert -- 34b-e --, therefor.

In Column 24, Line 27, Claim 24, delete "the contact" and insert -- the contact roller --, therefor.

Signed and Sealed this  
Eleventh Day of October, 2011

David J. Kappos  
*Director of the United States Patent and Trademark Office*

UNITED STATES PATENT AND TRADEMARK OFFICE
CERTIFICATE OF CORRECTION

PATENT NO.          : 7,879,008 B2
APPLICATION NO.     : 11/085616
DATED               : February 1, 2011
INVENTOR(S)         : Haury et al.

It is certified that error appears in the above-identified patent and that said Letters Patent is hereby corrected as shown below:

In Column 8, Line 49, delete "34l b-e" and insert -- 34b-e --, therefor.

In Column 23, Line 27, Claim 24, delete "the contact" and insert -- the contact roller --, therefor.

This certificate supersedes the Certificate of Correction issued October 11, 2011.

Signed and Sealed this
Twenty-eighth Day of August, 2012

David J. Kappos
*Director of the United States Patent and Trademark Office*